(12) United States Patent
Alagramam et al.

(10) Patent No.: US 10,561,636 B2
(45) Date of Patent: Feb. 18, 2020

(54) METHODS OF TREATING DISORDERS WITH GLYCOSYLATION DEFECTIVE PROTEINS

(71) Applicant: CASE WESTERN RERVE UNIVERSITY, Cleveland, OH (US)

(72) Inventors: Kumar N. Alagramam, Cleveland, OH (US); Suhasini Gopal, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/340,352

(22) PCT Filed: Oct. 10, 2017

(86) PCT No.: PCT/US2017/055914
§ 371 (c)(1),
(2) Date: Apr. 8, 2019

(87) PCT Pub. No.: WO2018/068051
PCT Pub. Date: Apr. 12, 2018

(65) Prior Publication Data
US 2019/0231741 A1   Aug. 1, 2019

Related U.S. Application Data

(60) Provisional application No. 62/405,351, filed on Oct. 7, 2016.

(51) Int. Cl.
| | |
|---|---|
| *A61K 31/12* | (2006.01) |
| *A61K 31/34* | (2006.01) |
| *A61K 31/335* | (2006.01) |
| *A61K 31/435* | (2006.01) |
| *A61K 33/00* | (2006.01) |
| *A61K 31/357* | (2006.01) |
| *A61K 31/365* | (2006.01) |

(52) U.S. Cl.
CPC .......... *A61K 31/357* (2013.01); *A61K 31/365* (2013.01)

(58) Field of Classification Search
CPC ...... A61K 31/12; A61K 31/34; A61K 31/335; A61K 31/435; A61K 33/00
USPC ......... 424/600; 514/299, 450, 456, 468, 679
See application file for complete search history.

(56) References Cited

U.S. PATENT DOCUMENTS

| | | | | |
|---|---|---|---|---|
| 5,219,880 A | * | 6/1993 | Thornfeldt | A61K 31/335 514/450 |
| 8,329,757 B2 | * | 12/2012 | Chen | A61K 31/18 514/678 |
| 2002/0147177 A1 | * | 10/2002 | Yuen | A61K 31/366 514/58 |

OTHER PUBLICATIONS

Alagrama et al. A small molecule mitigates hearing loss in a mouse model of Usher syndrome III, Nat. Chem. Biol., Jun. 2016, vol. 12, No. 6, pp. 444-451 (1-33).

Brostrom et al. Calcium dynamics and endoplasmic reticular function in the regulation of protein synthesis: implications for cell growth and adaptability, Cell Calcium, Oct.-Nov. 2003, vol. 34, No. 4-5, pp. 345-363.

* cited by examiner

*Primary Examiner* — Raymond J Henley, III
(74) *Attorney, Agent, or Firm* — Tarolli, Seundheim, Covell & Tummino LLP

(57) ABSTRACT

A method of treating a glycosylation-defective protein associated disease or disorder in a subject, the method includes administering to the subject a therapeutically effective amount of a Sarco/ER ATPase (SERCA) inhibitor.

22 Claims, 13 Drawing Sheets

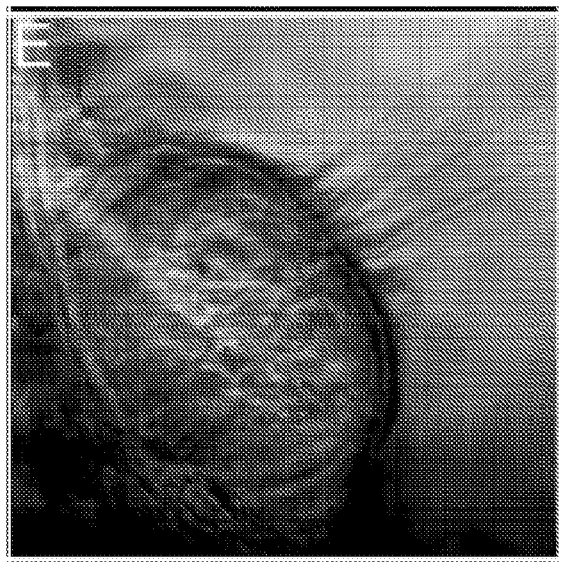
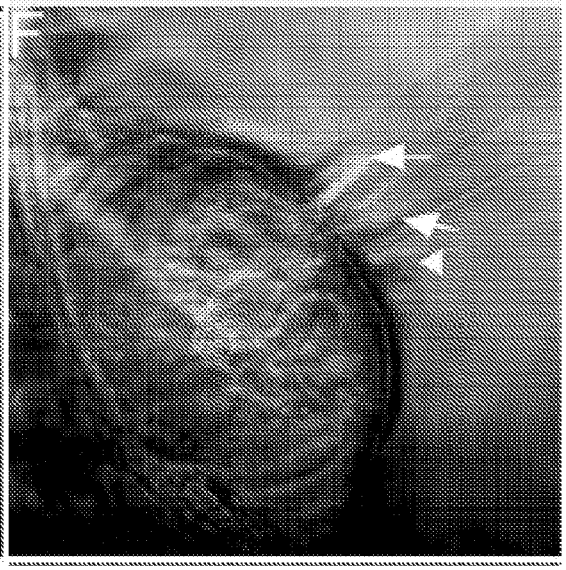
Fig. 1E  Fig. 1F
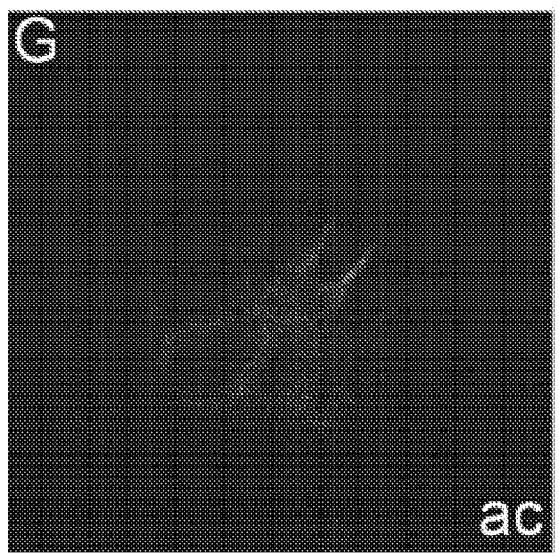
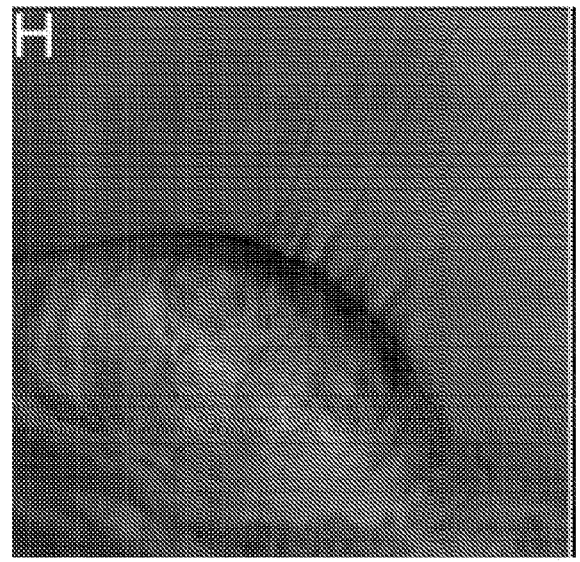
Fig. 1G  Fig. 1H

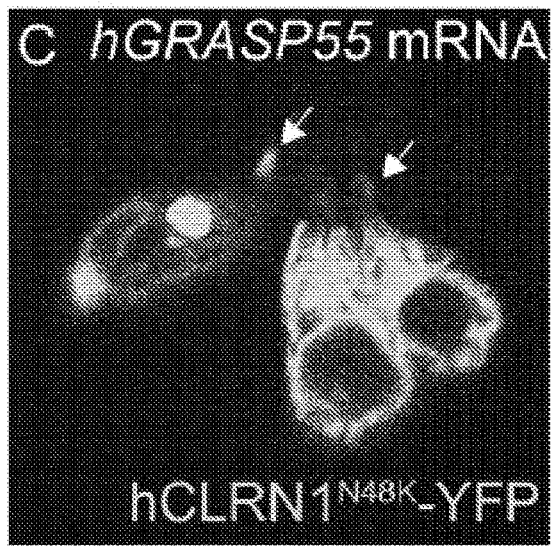
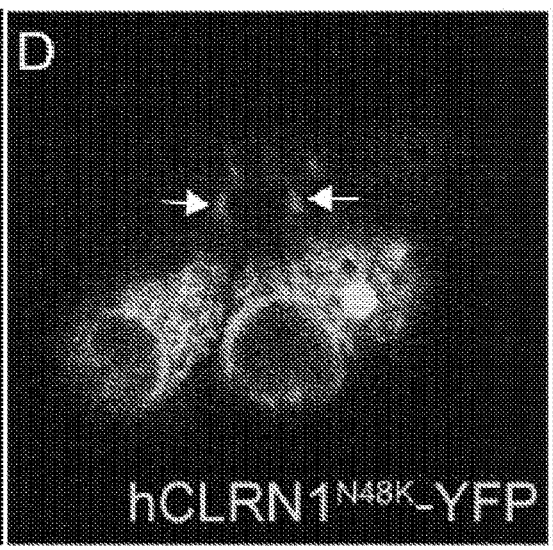
Fig. 3C
Fig. 3D
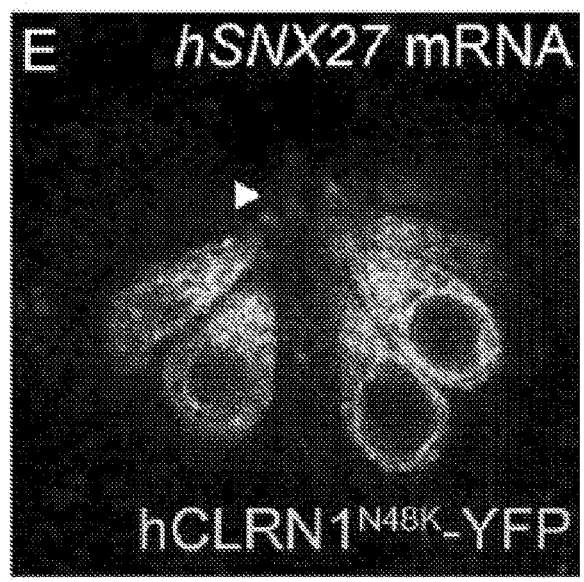
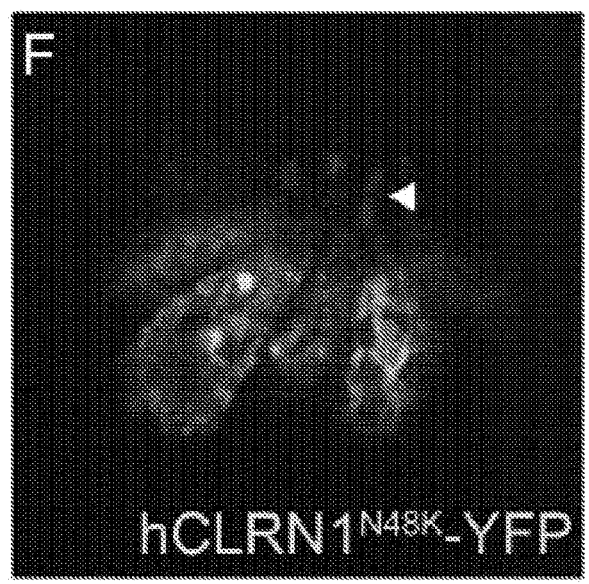
Fig. 3E
Fig. 3F

C

Stimulus 7 mm Hg

KO; *hCLRN1*-YFP

KO; *hCLRN1*$^{N48K}$-YFP

KO; *hCLRN1*$^{N48K}$-YFP (T)

5 μV 25 ms

METHODS OF TREATING DISORDERS WITH GLYCOSYLATION DEFECTIVE PROTEINS

RELATED APPLICATION

This application claims priority from U.S. Provisional Application No. 62/405,351, filed Oct. 7, 2016, the subject matter of which is incorporated herein by reference in its entirety.

GOVERNMENT FUNDING

This invention was made with government support under Grant No. R01 DC009246, awarded by The National Institutes of Health. The United States government has certain rights in the invention.

TECHNICAL FIELD

This application relates to methods of treating diseases and disorders that are associated with glycosylation-defective proteins in a subject, and more particularly to methods of treating diseases and disorders associated with glycosylation-defective protein misfolding and endoplasmic reticulum protein trapping in a subject in need thereof.

BACKGROUND

The hCLRN1$^{N48K}$ missense mutation is the most common Usher syndrome type III (USH3) causative mutation in North America and among those of Ashkenazi Jewish descent. A high incidence of inherited deaf-blindness in the Ashkenazi Jewish population can be attributed to the hCLRN1$^{N48K}$ mutation. For example, 40% of a cohort of 40 Jews with USH carried the hCLRN1$^{N48K}$ genotype. Despite a high incidence in the Ashkenazi Jewish population, USH3 is a rare disorder. No therapeutic options are available to prevent hearing or vision loss in hCLRN1$^{N48K}$ and devices such as cochlear implants and hearing aids have limitations.

There is no treatment for the eye disorder associated with USH3. USH3 patients having the hCLRN1$^{N48K}$ mutation are typically born with normal hearing and develop hearing loss in their teenage years. They learn to speak normally before their hearing declines and by middle age they are usually deaf. There is a window of opportunity to prevent deafness in hCLRN1$^{N48K}$ patients after early diagnoses and individuals at risk of developing the disease, based on DNA analysis or family history.

SUMMARY

Embodiments described herein relate to methods of treating diseases and disorder associated with glycosylation-defective proteins in a subject. The disease or disorder can include, for example, a disease or disorder associated with destabilizing mutations in the gene that encodes the human clarin-1 protein (hCLRN1). In some embodiments, the hCLRN1 destabilizing mutation is the missense mutation hCLRN1$^{N48K}$. In certain embodiments, the hCLRN1$^{N48K}$ associated disorder is Usher syndrome type III (USH3). The method of treating the disease or disorder in a subject can include administering to the subject a therapeutically effective amount of a SERCA inhibitor.

In some embodiments, the SERCA inhibitor is selected from the group consisting of Artemisinin, Artesunate (Arts), thapsigargin, mipsagargin, DBHQ (2,5-di-tert-butylhydroquinone), Saikosaponin-d (Ssd), SBF-1, ruthenium red, curcumin, F36, gingerol, paxilline, cyclopiazonic acid, sHA14-1, CXL017, analogs, and derivatives thereof.

In other embodiments, the SERCA inhibitor can be delivered to the subject by at least one of topical administration, systemic administration, transtympanic (or aka, intratympanic), intravitreal injection, and/or intraocular delivery.

Other embodiments relate to a method of treating a sensory deficit in a subject associated with a mutation of the human clarin-1 protein hCLRN1 protein. The method includes administering to the subject a therapeutically effective amount of a Sarco/ER ATPase (SERCA) inhibitor. In some embodiments, the sensory deficit includes hearing loss. The therapeutically effective amount can include the amount required to promote hCLRN1$^{N48K}$ localization to hair bundles of a hair cell (the sensory cell in the inner ear) without affecting the viability of the hair cell.

Still other embodiments relate to a method of treating Usher syndrome type III (USH3) in a subject. The method includes administering to the subject a therapeutically effective amount of a Sarco/ER ATPase (SERCA) inhibitor. In some embodiments, the USH3 is associated with a human clarin-1 protein (hCLRN1) missense mutation. The hCLRN1 missense mutation can include hCLRN1$^{N48K}$. In some embodiments, the SERCA inhibitor is administered prior to sensory deficit in the USH3 subject.

DETAILED DESCRIPTION

Figure 1A:
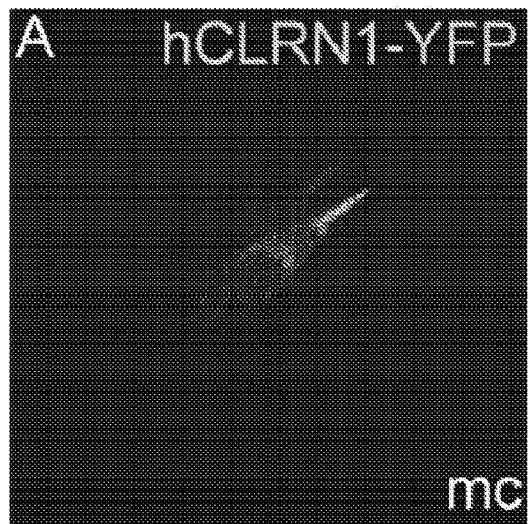
FIGS. 1(A-L) illustrate images showing rescue of the morphological defects of hair bundle in clrn1$^{KO/KO}$ mutant by hCLRN1. Hair cells expressing hCLRN1-YFP in the medial cristae (A) and (D) showed cone-shaped (wild-type) hair bundle morphology whereas surrounding (YFP-negative) hair cells showed splayed hair bundle morphology, as revealed by the DIC (B, E) and merged (C, F) images. (G-L) The hair bundle morphology was uniformly rescued in all hair cells in stable transgenic lines expressing hCLRN1-YFP in the clrn1$^{KO/KO}$ background. Hair cells from anterior crista (G) and medial crista (J) display expression of hCLRN1-YFP in all hair bundles. DIC images reveal cone-shaped bundles across both cristae (H and K), and merged images (I and L) confirm colocation of the YFP signal and cone-shaped bundles. It should be noted that both in the transient and stable expression lines, the hCLRN1-YFP predominantly localizes to the hair bundle (A, D, G, J). Magnification, 63×. (All images captured from live larvae and all images shown here are single plane images from 6 days post fertilization (dpf) larvae, and are 1 (micrometer) M middle section of the crista).
Figure 1B:
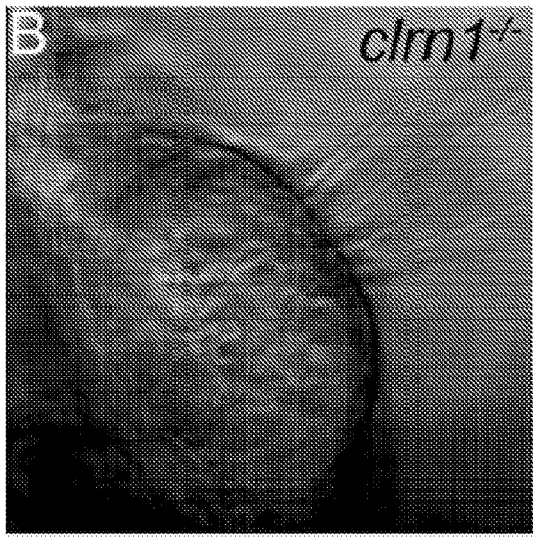
Figure 1C:
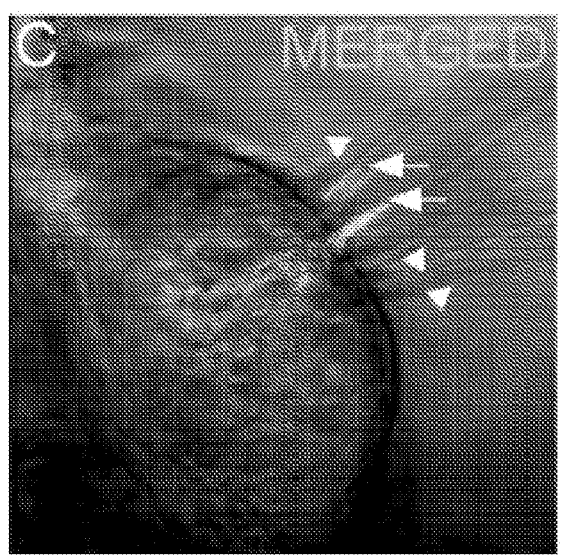
Figure 1D:
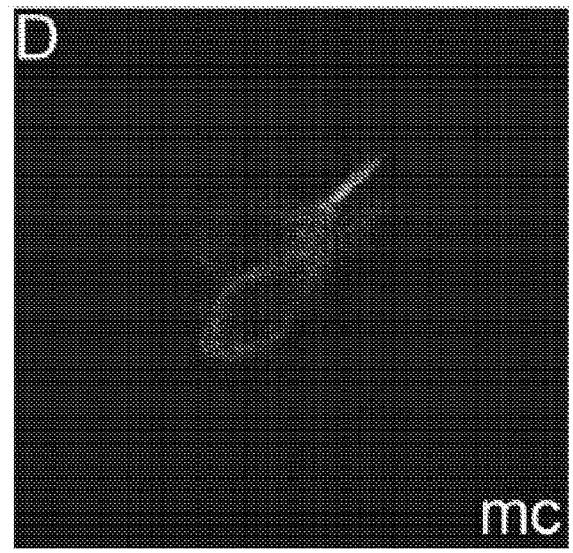
Figure 1I:
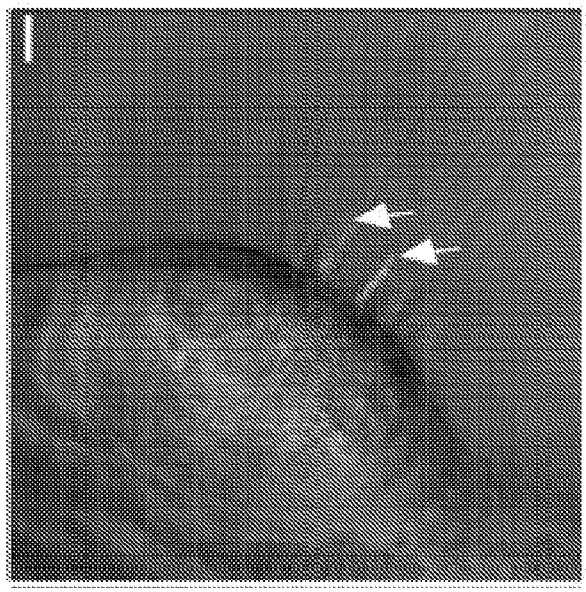
Figure 1J:
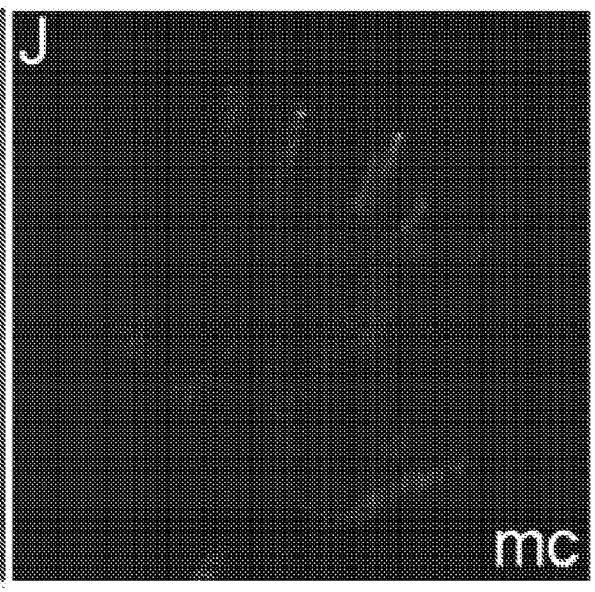
Figure 1K:
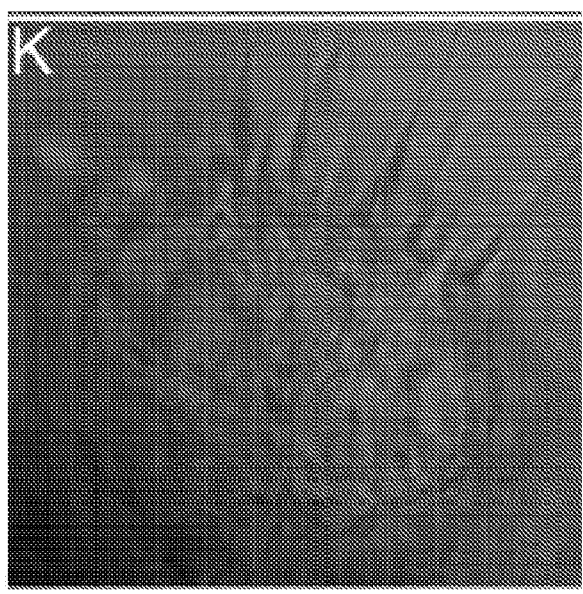
Figure 1L:
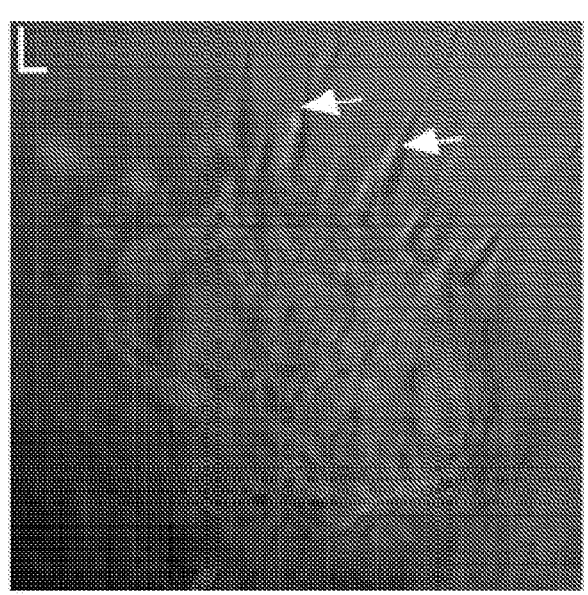
Figure 2A:
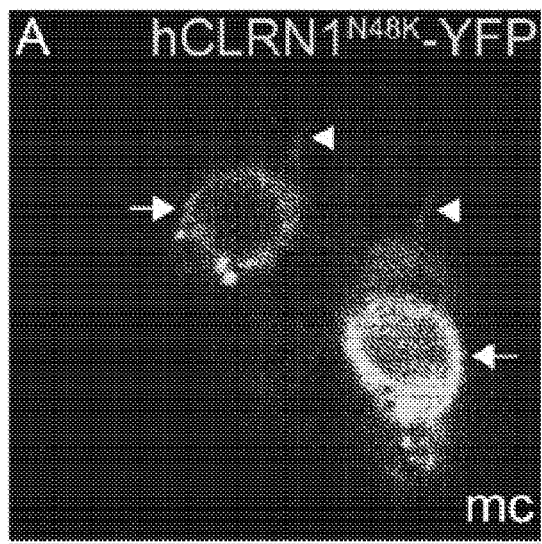
FIGS. 2(A-F) illustrate images showing hair bundle localization of hCLRN1$^{N48K}$ rescues the morphological defects of hair bundle in clrn1$^{KO/KO}$ mutant. (A-F) clrn1$^{KO/KO}$ mutants stably expressing the pathogenic form of human clarin-1 fused to YFP (hCLRN1$^{N48K}$-YFP) in hair cells showed the majority of the mutant protein mislocalized (remain intracellular, arrow); and relatively small amount reaches the hair bundle (arrowhead). Representative images of hair cells from the medial crista (A) and anterior crista (D) are shown here. Though hCLRN1$^{N48K}$-YFP expression is relatively weak in the hair bundle compared to its wild-type counterpart (FIG. 1), the hair bundle morphology defect associated with clrn1$^{KO/KO}$ mutation is rescued in the anterior crista (A) and posterior crista (D) (arrowhead in A and D). DIC (B and E) and merged (C and F) reveal YFP signal coincides with the cone-shaped bundle morphology, indicating rescue of hair bundle morphology in the presence of hCLRN1$^{N48K}$ in the bundle. Magnification, 40×. (All images captured from live larvae and all images shown here are single plane images from 6 dpf larvae, and are 1 μM middle section of the crista).
Figure 2B:
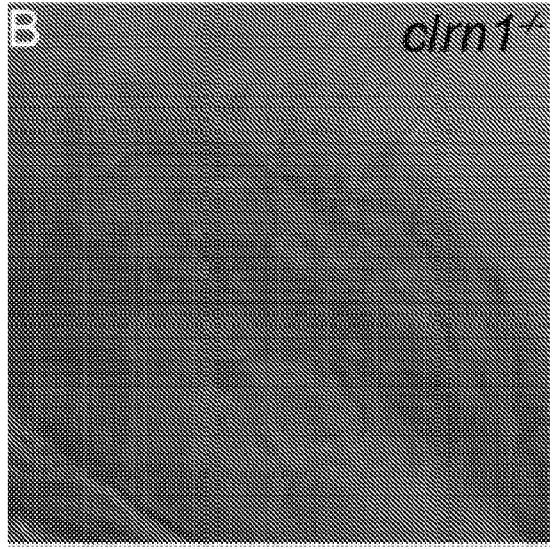
Figure 2C:
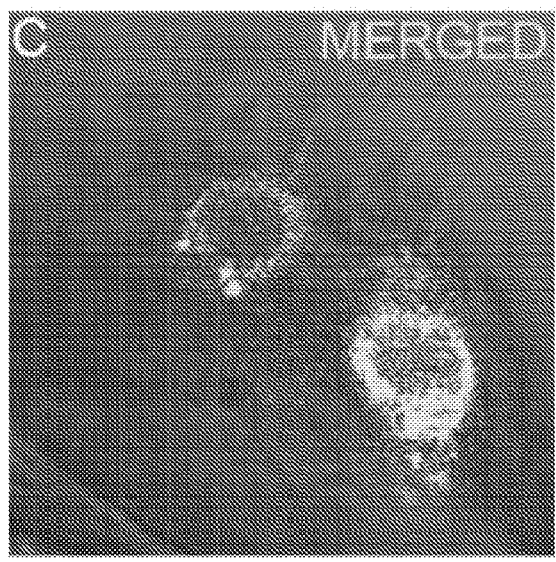
Figure 2D:
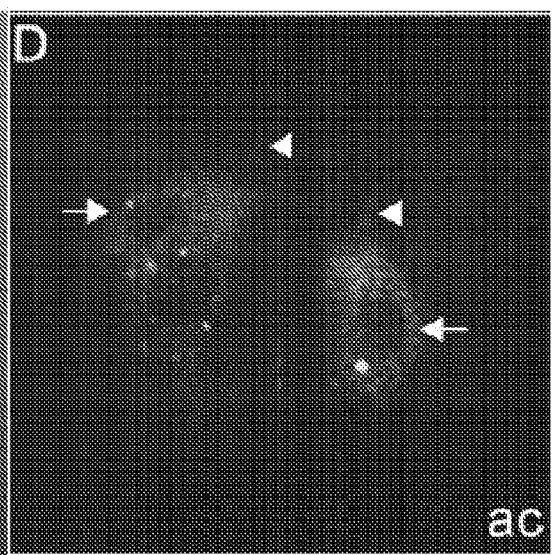
Figures 2E, 2F:
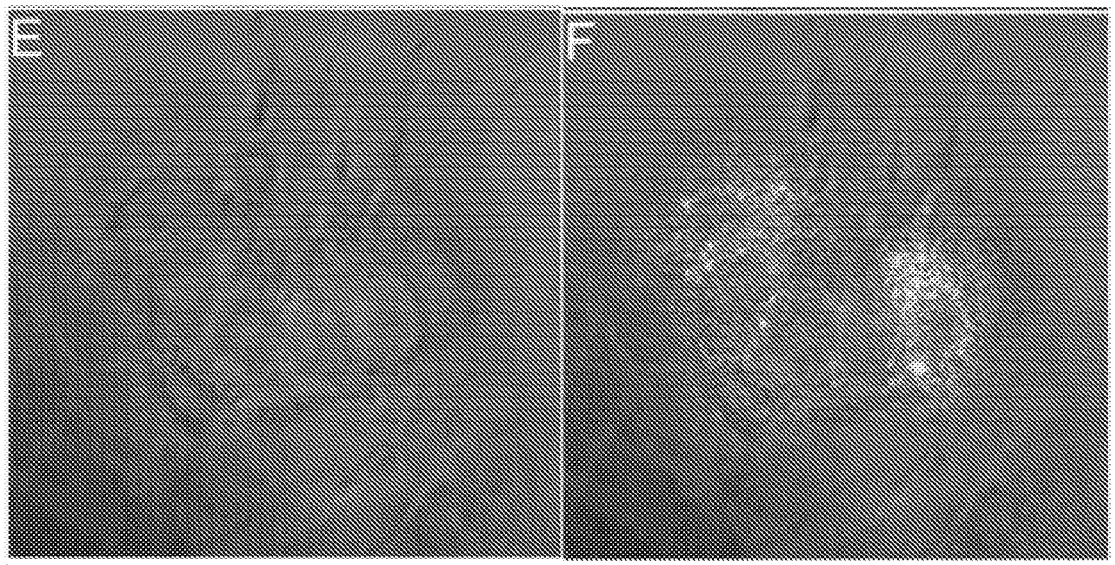

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The phrases "parenteral administration" and "administered parenterally" refer to modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" refers to inhibiting a disease, disorder or condition in a subject, e.g., impeding its progress; and relieving the disease, disorder or condition, e.g., mitigating causing regression of the disease, disorder and/or condition. Treating the disease or condition includes ameliorating or mitigating at least one symptom of the particular disease or condition, even if the underlying pathophysiology is not affected.

The term "preventing" refers to stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term a "pharmaceutical composition" refers to a formulation containing the disclosed compounds in a form suitable for administration to a subject. The pharmaceutical composition can be in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including ocular, otic, oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" refers to a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated within the scope of the claims.

The phrase "pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

It should be understood that all references to pharmaceutically acceptable salts include solvent addition forms (solvates) or crystal forms (polymorphs) as defined herein, of the same salt.

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present application is intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds described herein wherein a hydroxy, amino, sulfhydryl, carboxy, or carbonyl group is bonded to any group that may be cleaved in vivo to form a free hydroxyl, free amino, free sulftydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds described herein, and the like (e.g., Bundegaard, H. "Design of Prodrugs" p 1-92, Elesevier, New York-Oxford (1985)).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2$^{nd}$ ed. 1991); Harrison and Harrison et al., Compendium of Synthetic Organic Methods, Vols. 1-8 (John Wiley and Sons, 1971-1996); and Kocienski, Protecting Groups, (Verlag, 3$^{rd}$ ed. 2003).

The term "amine protecting group" refers to a functional group that converts an amine, amide, or other nitrogen-containing moiety into a different chemical group that is substantially inert to the conditions of a particular chemical reaction. Amine protecting groups can be removed easily and selectively in good yield under conditions that do not affect other functional groups of the molecule. Examples of amine protecting groups include, but are not limited to, formyl, acetyl, benzyl, t-butyldimethylsilyl, t-butdyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other amine protecting groups can be identified by those of skill in the art.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" refers to solvent addition forms that contain either stoichiometric or non stoichiometric amounts of solvent. Some compounds have a tendency to trap a fixed molar ratio of solvent molecules in the crystalline solid state, thus forming a solvate. If the solvent is water, the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrate.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

The term "derivative", refers to a compound that may be produced from another compound having a common core structure in one or more steps through the substitution of various groups, as in replacement of H by an alkyl, acyl, amino group.

A "patient," "subject," or "host" to be treated by the subject method may mean either a human or non-human animal, such as primates, mammals, and vertebrates.

The term "prophylactic or therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" refer to molecules and other agents that are biologically, physiologically, or pharmacologically active substances that act locally or systemically in a patient or subject to treat a disease or condition, such as diseases or disorders whose etiology includes glycosylation-defective proteins (e.g., hCLRN1$^{N48K}$ in hair cells of the ear or retinal cells of the eye?) in the subject. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" is an art-recognized term. In certain embodiments, the term refers to an amount of a therapeutic agent that, when incorporated into a polymer, produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" refer to the dose of a drug, which produces 50% of its maximum response or effect, or alternatively, the dose, which produces a pre-determined response in 50% of test subjects or preparations. The term "LD50" refers to the dose of a drug, which is lethal in 50% of test subjects. The term "therapeutic index" refers to the therapeutic index of a drug, defined as LD50/ED50.

"Stable compound" and "stable structure" are meant to indicate a compound that is sufficiently robust to survive isolation, and as appropriate, purification from a reaction mixture, and formulation into an efficacious therapeutic agent.

"Free compound" is used herein to describe a compound in the unbound state.

In the specification, the singular forms also include the plural, unless the context clearly dictates otherwise. Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

All percentages and ratios used herein, unless otherwise indicated, are by weight.

Embodiments described herein relate to methods of treating diseases and disorders associated with glycosylation-defective proteins in a subject in need thereof by administering to the subject a Sarco/Endoplasmic Reticulum ATPase (SERCA) inhibitory compounds.

Glycosylation is the most common chemical process of protein modification and occurs in every living cell. Generally, disturbances of glycosylation may be either congenital or acquired. Correct glycosylation is essential for obtaining (for example, proper localization of hCLRN1 to the plasma membrane in a cell) and supporting a normal biological activity of proteins, and its impairment leads to the synthesis of glycoproteins with reduced or lost function. In some cases, disturbances of glycosylation result from genetic defects leading to the deficiency or loss of enzyme activity involved in glycan synthesis and processing, or to deficiency of specific transporters. These defects have been found in the activation, presentation, and transport of sugar precursors, in the enzymes responsible for glycosylation, and in proteins that control the traffic of component. These genetic defects cause severe multiorgan and multisystem disorders having clinical features involving many system organs, but specifically relate to the development of certain regions of the brain and functions of the gastrointestinal, hepatic, visual, auditory and immune systems.

Sarco/ER ATPase (SERCA) transports calcium ions into the ER and is important in the regulation of intracellular calcium levels. SERCA inhibitors have been shown to induce increases in cytosolic calcium levels and perturb ER by triggering ER stress and unfolded protein response (UPR).

It was found that SERCA inhibitors can liberate deleterious glycosylation-defective misfolded proteins that accumulate in the endoplasmic reticulum (ER) of a subject's cells that are associated with and/or causative of the disease or disorder. The Example described herein shows that SERCA inhibitors can rescue destabilizing mutations in the gene that encodes the human clarin-1 protein (hCLRN1), a protein that carries the missense mutation hCLRN1$^{N48K}$, which results in glycosylation deficient clarin-1 protein leading to aggregation in the ER. SERCA inhibitors delivered to sensory cells were found to liberate hCLRN1$^{N48K}$ providing an opportunity for therapeutic intervention in Usher syndrome patients before the onset of sensory deficits such as deafness and blindness in the patients.

In some embodiments, the glycosylation-defective protein associated disease or disorder that is treated by administration of the SERCA inhibitor can include, for example, a disease or disorder associated with destabilizing mutations in the gene that encodes the human clarin-1 protein (hCLRN1) leading to protein aggregation in the ER. In some embodiments, the hCLRN1 destabilizing mutation is the missense mutation hCLRN1$^{N48K}$. In certain embodiments, the hCLRN1$^{N48K}$ associated disorder is Usher syndrome type III (USH3).

Additional glycosylation-defective protein associated diseases or disorders can include, but are not limited to those related to: type I and II congenital disorders of glycosylation (CDG), COG8 deficiency, COG1 deficiency, RFT1 deficiency, Oligosaccharyl transferase subunits TUSC3 and IAP, Dolichol kinase deficiency, Vacuolar ATPase, Mucolipodoses II and III; Muscular dystrophies, such as Walker-Warburg syndrome, Muscle-eye-brain disease, Fukuyama muscular dystrophy, Congenital muscular dystrophy types 1C and 1D, Hereditary inclusion body myopathy-II; Glycosamino glycan defects, such as Ehlers-Danlos syndrome, Hereditary multiple exostosis, Chondrodysplasias, Spondyloepimetaphyseal dysplasia, Molecular corneal dystrophy types I and II, and Schneckenbecken dysplasia; Glycosphingolipid defects, such as Amish infantile epilepsy; O-GalNAc defects, such as Tn syndrome, and Familial timorous calcinosis; GPI anchor defects, such as Paroxysmal nocturnal hemoglobinuria, and autosomal recessive GPI anchor deficiency; and additional disorders, such as Peters plus syndrome, Congenital dyserythropoietic anemia (CDA typeII, HEMPAS), and neurodegenerative diseases, such as Alzheimer's disease.

Other embodiments relate to a method of treating a sensory deficit in a subject associated with a mutation of the human clarin-1 protein hCLRN1 protein. The method includes administering to the subject a therapeutically effective amount of a SERCA inhibitor. A sensory deficit can include hearing and/or vision loss in the subject. In certain embodiments, the sensory deficit is hearing loss. In some embodiments, the SERCA inhibitor can promote hCLRN1$^{N48K}$ localization to hair bundles of a hair cell without affecting the viability of the hair cell in the subject.

The SERCA inhibitors for use in the methods described herein can include any compound that can inhibit SERCA activity and liberate glycosylation defective misfolded proteins trapped in the endoplasmic reticulum that are at least partially causative of a glycosylation-defective protein associated disease or disorder, such as Usher syndrome. In some embodiments, the SERCA inhibitor can be selected from sesquiterpene lactones and derivatives thereof (compounds built from 3 isoprene units and containing a lactone ring), such as thapsigargin and prodrug thereof, such as 8-O-(12Aminododecanoyl)-8-0 debutanoylthapsigargin (G202) and the peptide prodrug L12ADT and, artemisinin, artemisinin analogs and derivatives thereof; hydroquinone based compounds such as 2,5-di(tert-butyl)hydroquinone (BHQ); 1,3-dibromo-2,4,6-tris(methyl-isothio-uronium)benzene, celecoxib cyclopiazonic acid; clotrimazole, thioronium benzene derivatives, tetrabromobisphenol, polyphenols and curcumin. For example, Michelangeli et al. 2011 discloses 1,3-dibromo-2,4,6-tris(methylisothiouronium)benzene (Br2-TITU), 2APB, 3,6-dihydroxyflavone, 4-chloro-m-cresol, alisol B, BHQ, bisphenol, bisphenol A, calmidazolium, chlorpromazine, curcumin, cyclopiazonic acid, A, DES, fluphenazine, galangin, ivermectin, mastoparan, nonylphenol, orthovanadate, paxilline, peptide M391, quercitin, eapamycin, sHA 14-1, TBBPA, and thapsigargin as compounds that act as SERCA inhibitors. Other examples of SERCA inhibitors include, but are not limited to, G-115 (U.S. Pat. No. 7,635,682), ruthenium red (Charuk et al. 1990) CXL017 (Bleeker et al. 2013), Saikosaponin-d (Wong et al. 2013), and artemisinins (Eckstein-Ludwig et al. 2003). Further examples are disclosed in US2010087374 and WO2010088450.

Examples of Atemisinin analogs and derivatives are described in US Patent App. No. 20060142377A1, the subject matter of which is incorporated herein by reference in its entirety.

In one embodiment, the SERCA inhibitor is the Artemisinin derivative, Artesunate (Arts), which has the formula:

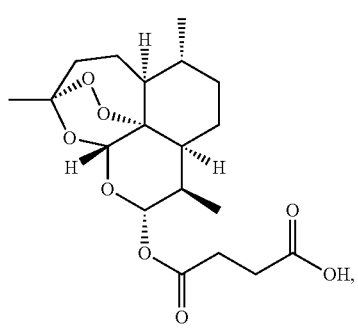 [SMILES: C[C@H]1[C@H](OC(=O)CCC(=O)O)O[C@@H]2O[C@@]3(C)CC[C@H]4[C@H](C)CC[C@@H]1[C@@]24OO3]

and pharmaceutically acceptable salts thereof.

In other embodiments, SERCA inhibitors administered to a subject for the treatment of diseases and disorders associated with glycosylation-defective proteins in a subject described herein can include thapsigargin, analogs and derivatives thereof, such as mipsagargin.

The SERCA inhibitor used in methods described herein can be administered to the subject to treat a disease or disorder associated with a glycosylation-defective protein using standard delivery methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Treatment according to the method described herein can be altered, stopped, or re-initiated in a subject depending on the status of disease or disorder. Treatment can be carried out as intervals determined to be appropriate by those skilled in the art. For example, the administration can be carried out 1, 2, 3, or 4 times a day. In another embodiment, the SERCA inhibitor can be administered prior to sensory deficit related to a glycosylation-defective protein has occurred. In certain embodiments, the SERCA inhibitor can be administered to a subject prior to a sensory deficit, such as hearing loss, in the subject having USH3.

The treatment methods can include administering to the subject a therapeutically effective amount of a SERCA inhibitor. Determination of a therapeutically effective amount is within the capability of those skilled in the art. The exact formulation, route of administration, and dosage can be chosen by the individual physician in view of the subject's condition.

In some embodiments, the therapeutically effective amount is the amount required to increase in cytosolic calcium levels and perturb ER in a subject's cells, thereby triggering and ER stress and unfolded protein response (UPR) in the cells. In some embodiments, the therapeutically effective amount is the amount required to liberate/rescue glycosylation-defective proteins (e.g., hCLRN1$^{N48K}$) trapped in the endoplasmic reticulum of a subject's cells and allowing for protein translocation of the defective protein in the cell. For example, in certain embodiments, the therapeutically effective amount is the amount required to promote hCLRN1$^{N48K}$ localization to hair bundles of a hair cell. In some embodiments, the therapeutically effective amount is the amount effective in a method described herein without affecting the viability of a cell (e.g., a sensory cell, such as a hair cell) in the subject. In some embodiments, the therapeutically effective amount is the amount required to mitigate sensory deficits such as hearing and vision loss associated with destabilizing mutations in hCLRN1 in subjects, for example those subjects having USH3.

Formulation of pharmaceutical compounds for use in the modes of administration noted above (and others) are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In one example, the SERCA inhibitor compound can be provided in an otic preparation that can be administered to the subject's ear. For example, an otic preparation including a SERCA inhibitor can be administered to the outer, middle, or inner ear.

Administration to the outer are can be accomplished using local administration of an otic preparation (e.g., ear drops or ointment). Otic preparation can be administered to the middle ear through the use of injections through the tympanic membrane or using fixed catheters or wicks through the tympanic membrane for repeated administration at regular intervals. In order to decrease drainage of an otic preparation through the Eustachian tube, the viscosity of liquid formulations can be increased with solvents such as glycerin or propylene glycol; polymers such as sodium hyaluronate, gelatin, or polypropylene fumarate, or other biodegradable polymers.

In some embodiments, Auricular (Otic) preparations can be administered to the inner ear of the subject. Inner ear drug delivery can include intratympanic and intracochlear delivery. Strategies for drug delivery to the inner ear are reviewed by Liu et al., (2013) Acta Pharmaceutica Sinica B, 3(2): 86-96, the subject matter of which is incorporated herein by reference in its entirety.

Intratympanic delivery to the inner ear was performed via the injection or perfusion of the drug to the middle ear with the aim of drug diffusion through the round window membrane (RWM) into the inner ear. This approach possesses several advantages over systemic drug delivery as this local drug delivery method can bypass the blood labyrinth barrier (BLB), and therefore result in higher drug concentrations in the inner ear fluids and avoid undesired systemic exposure. Effective drug delivery to the inner ear via the intratympanic route also relies on the contact time of the drug solution (or drug delivery system) with the RWM. Unfortunately, large portions of the administered drugs are usually eliminated through the Eustachian tube following intratympanic drug delivery. To overcome this limitation devices and sustained-release drug delivery systems can be employed.

Examples of intratympanic approaches to inner ear drug delivery include cannula-based delivery systems, such as a Silverstein microwick and a round window microcatheter. Another example of an intratympanic approach to inner ear drug delivery can include sustained-release systems. Sustained-release drug delivery systems can increase the residence time of a drug in the middle ear and provide controlled drug delivery to the inner ear. Sustained-release drug delivery systems can include the use of hydrogels and nanoparticles and generally sustain drug delivery by the mechanisms of slow degradation of the material, slow drug diffusion, or a combination of both.

Direct intracochlear drug delivery can bypass the middle ear and allow drugs to get to their intended sites directly. Intracochlear delivery can substantially increase drug bioavailability in the inner ear and has the highest efficiency among the inner ear delivery methods. Numerous intracochlear delivery technologies have been developed to improve the efficiency of drug delivery to the inner ear. They include direct injections, cochlear implants, osmotic mini-pumps, as well as reciprocating perfusion systems. Direct injection is the injection of drug solution directly into the cochlea through the RWM with a microsyringe and a narrow-gauge needle. This provides accurate drug delivery for acute drug application to the base of the cochlea. Cochlear implant is a device inserted into the scala tympani in the treatment of inner ear disorders. The basic mechanism behind this treatment is to directly simulate spiral ganglion neurons with electrical pulses through an electrode, overcoming the loss of hair cells in the cochlea. Cochlear implant can be combined with concurrent use of drugs with implant to reduce trauma to the inner ear or to prevent further degeneration of hearing after implantation. Osmotic mini-pumps are used to directly deliver drugs into ST via cannula, and reciprocating perfusion systems are similar to osmotic mini-pumps with the main difference that there is no accompanying net volume change of fluid in the reciprocating perfusion systems.

In another example, the SERCA inhibitor compound can be provided in an ophthalmic preparation that can be administered to the subject's eye. The ophthalmic preparation can contain the SERCA inhibitor in a pharmaceutically acceptable solution, suspension or ointment. Some variations in concentration will necessarily occur, depending on the particular SERCA inhibitor employed, the condition of the subject to be treated and the like, and the person responsible for treatment will determine the most suitable concentration for the individual subject.

The ophthalmic and otic preparations can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose. In some embodiments, the ophthalmic or otic preparation can be administered topically to the eye of the subject in need of treatment by conventional methods, for example, in the form of drops or by bathing the eye in the ophthalmic solution.

The SERCA inhibitor can also be formulated for topical administration through the skin. "Topical delivery systems" also include transdermal patches containing the ingredient to be administered. Delivery through the skin can further be achieved by iontophoresis or electrotransport, if desired.

Formulations for topical administration to the skin can include, for example, ointments, creams, gels and pastes comprising SERCA inhibitor in a pharmaceutical acceptable carrier. The formulation of the primary amine compound for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Subjects affected with or at risk of a glycosylation-defective protein associated disease or disorder, which are not readily accessible or suitable for ophthalmic (e.g. eye-drops), otic and/or topical administration, can be treated by a systemic approach, such as intravenous infusion. For example, the SERCA inhibitor can be administered at a low dosage by continuous intravenous infusion. In another example, in which a patient requires longer-term care, the SERCA inhibitor can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the SERCA inhibitor to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the SERCA inhibitor.

As discussed above, a SERCA inhibitor may be administered to a subject in order to treat or prevent sensory deficit whose etiology involves a mutation of the human clarin-1 protein hCLRN1 protein in a subject. Other diseases, disorders, or conditions characterized by a glycosylation-defective protein may be similarly treated.

In one embodiment, a subject is diagnosed as having symptoms of a glycosylation-defective protein associated disease or disorder, and then a disclosed SERCA inhibitor compound is administered. In some embodiments, the subject administered a SERCA inhibitor in a method described herein are individuals following an early diagnosis and individuals at risk of developing a glycosylation-defective protein associated disease or disorder. The risk of developing the disease can be determined using various known methods such as, but not limited to, DNA analysis and/or family history.

In another embodiment, a subject may have a sensory deficit associated with a glycosylation-defective protein in both eyes or both ears, and then a disclosed SERCA inhibitor is administered. In another embodiment, a subject may have a sensory deficit in one eye or ear but not in the other eye or ear, and then a disclosed SERCA inhibitor is administered. In yet another embodiment, a subject may be diagnosed as having USH3 and then a disclosed SERCA inhibitor is administered. In another embodiment, a subject is diagnosed as having symptoms of other forms of disease whose etiology involves glycosylation-defective protein in ocular or otic tissue cells of a subject, and then the SERCA inhibitor is administered. In another embodiment, a subject may be identified as being at risk for developing other forms of sensory deficit whose etiology involves a mutation of the human clarin-1 protein hCLRN1 protein in ocular or otic tissue cells, and then a disclosed SERCA inhibitor is administered. In some embodiments, a SERCA inhibitor is administered prophylactically. In some embodiments, a subject has been diagnosed as having a disease before a sensory deficit is apparent (e.g., prior to hearing and/or vision loss).

In some embodiments, a subject may be monitored for the extent of sensory deficit. A subject may be monitored in a variety of ways, such as by eye examination, dilated eye examination, Electroretinogram (ERG), fundoscopic examination, visual acuity test, ear examination, auditory acuity test, audiometric test, balance testing, and/or biopsy. Monitoring can be performed at a variety of times. For example, a subject may be monitored after a SERCA inhibitor administered. The monitoring can occur, for example, one day, one week, two weeks, one month, two months, six months, one year, two years, five years, or any other time period after the first administration of a SERCA inhibitor. A subject can be repeatedly monitored. In some embodiments, the dose of a compound may be altered in response to monitoring.

In some embodiments, the disclosed methods may be combined with other methods for treating or preventing a glycosylation-defective protein associated disease or disorder or other forms of disease whose etiology involves a mutation of the human clarin-1 protein hCLRN1 protein in sensory tissue cells. For example, a subject may be treated with more than one therapy for one or more diseases or disorders. For example, a subject having USH3 can be treated with or assisted with the use of assistive listening devices (e.g., headsets, microphones, hearing aids, specifically adapted phones and others devices, which amplify the sounds of conversation between a listener and a talker), Braille or sign language instruction, cochlear implants, orientation and mobility training, and/or auditory (hearing) training.

Usher syndrome affects the retina's light-sensing cells called rods and cones. This condition is called retinitis pigmentosa or RP. In RP, the retina's light-sensing rods and cones slowly go bad, starting at the outer edges. As RP gets worse, the person loses peripheral (edges) vision first then central vision. Therefore, in some embodiments, an additional treatment of vision loss associated with USH3 can include the administration of high doses Vitamin A palmitate, which has been shown to slow down changes in the eye due to RP.

In yet another embodiment, the SERCA inhibitor compound described herein can be administered as part of a combinatorial therapy with additional therapeutic agents. The phrase "combinatorial therapy" or "combination therapy" embraces the administration of a SERCA inhibitor, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, ocular routes, otic routes, oral routes, intravenous routes, intramuscular routes, and direct absorption through mucous membrane tissue. The therapeutic agents can be administered by the same route or by different routes. The sequence in which the therapeutic agents are administered is not narrowly critical.

The invention is further illustrated by the following example, which is not intended to limit the scope of the claims.

EXAMPLE

Hereditary hearing loss (HHL) is a common sensory disorder often linked to defects in the mechanosensory 'hair' cells of the inner ear. HHL is frequently associated with recessive inheritance of a point mutation that result in either attenuation or loss of gene function in hair cells. In vivo models with mutation in the orthologous genes are typically used to shed light on the possible function of the wild type (WT) human gene in hair cells and the mechanism underlying the pathogenic variant. Nevertheless, direct investigation of human protein and its pathogenic variant in hair cells in an in vivo setting would significantly enhance our ability to validate protein function, investigate pathogenic mechanism and identify drugs that mitigate the pathogenic effect. A paradigm for this scenario is the Usher syndrome III (USH3) causative gene product CLRN1$^{N48K}$. Due to a missense mutation in the clarin-1 (CLRN1) gene, the amino acid asparagine (N) at position 48 is replaced by lysine (K) in the human clarin-1 (hCLRN1) protein (Joensuu et al., 2001; Adato et al. 2002; Ness et al., 2003; Plantinga et al., 2005). Individuals, homozygous for the recessive CLRN1$^{N48K}$ mutation develop vision and hearing at birth but fail to retain these function with age (Ness et al 2003), suggesting hCLRN1-mediated function is expressed early on but diminishes overtime. We developed a model system to investigate the function of hCLRN1 and defects due to hCLRN1$^{N48K}$ in hair cells in vivo. The model systems we generated are amenable to biochemical and genetic interrogation to test mechanistic hypotheses related to the pathogenic variant. Details about the models and results from these investigations are reported here.

Both, mouse (Clrn1$^{KO/KO}$) and zebrafish (clrn1$^{KO/KO}$) models for clarin-1 null mutation and Clrn1$^{N48K/N48K}$ mouse models show disruption in the hair bundle structure and attenuation of the mechanosensory function of the hair cells, suggesting loss of hair cell function to be the cause of hearing loss in the USH3 individuals. The hair bundle phenotype in clarin-1 mutants suggests that maintenance of the actin-rich core of stereocilia in the hair bundle may be dependent on clarin-1 localization to the hair bundle. This speculations is consistent with findings that hCLRN1 expressed in the HEK293 cells are associated with membranous microdomain that are involved in the activation of actin polymerization. Together these findings led us to hypothesis that clarin-1 plays an important role in the maintenance of actin-rich core of the hair bundle, and loss of clarin-1 results in the disruption of hair bundle structure and hair cell function.

We showed that hCLRN1 localize to the hair bundle using a transgenic zebrafish (clrn1$^{+/+}$) stably expressing hCLRN1 fused with yellow fluorescence protein (YFP), hCLRN1-YFP, in hair cells. Though, hCLRN1 is known to be a protein of membranous microdomain that activates actin polymerization and localize to the hair bundle, still it is not clear whether like mouse and zebrafish, hCLRN1 is required for hair bundle maintenance and function. Here, we tested this hypothesis by considering whether hCLRN1 function is conserved across species. If true, substituting hCLRN1 in the hair cells of clrn1$^{KO/KO}$ zebrafish (hCLRN1-YFP; clrn1$^{KO/KO}$) should preserve the normal hair bundle structure and function. If the function of hCLRN1 is conserved, then similar model with hCLRN1$^{N48K}$ expressed in hair cells of clrn1$^{KO/KO}$ zebrafish (hCLRN1$^{N48K}$-YFP; clrn1$^{KO/KO}$) will be a novel tool to, A) directly investigate the pathogenic mechanism associated with the hCLRN1$^{N48K}$ protein in live hair cells and B) identify drugs that rectify the phenotype associated with this mutation.

Individuals recessive for the hCLRN1$^{N48K}$ mutation are born hearing, but auditory function is lost over time, suggesting that these individuals develop functional hair cells but fail to maintain them. The pathogenic mechanism of progressive hearing loss in these individuals is not known. In the transgenic hCLRN1$^{N48K}$-YFP; clrn1$^{+/+}$ zebrafish expressing hair cell specific hCLRN1$^{N48K}$-YFP, the mutant protein largely remained intracellular with a marginal amount of fluorescence detected in the hair bundle. Previous studies on hCLRN1$^{N48K}$ using HEK293 cells have also shown that loss of N-glycosylation site in hCLRN1$^{N48K}$ results in the mutant protein been trapped in endoplasmic reticulum (ER) followed by ER-associated degradation (ERAD). We previously proposed an hypothetical model for progressive hearing loss in the hCLRN1$^{N48K}$ USH3 individuals namely, the availability of hCLRN1$^{N48K}$ in the hair bundle diminishes over time, due to ER accumulation and intracellular degradation of the mutant protein, and the ability of the protein to deliver clarin-1-mediated function (if transported to the bundle) is not compromised by the N48K mutation. Importantly, our recent findings based on a small molecule BF844's ability to mitigate hearing loss in a mouse model for progressive hearing loss associated with the hCLRN1$^{N48K}$ mutation (the TgAC1; Clrn1$^{N48K/N48K}$ mouse model) also confirms that N-glycosylation mutation (N48K) in the clarin-1 protein does not affect its function. In the current study, to test the hypothesis that the progressive loss of hearing in a subset of USH3 individuals are due to defect in hCLRN1$^{N48K}$ protein localization to the hair bundle and not due to compromise in the function, we generated a clrn1$^{KO/KO}$ zebrafish stably expressing hCLRN1$^{N48K}$ in the hair cells, and longitudinally studied the structural and functional changes in hair cells associated with the hCLRN1$^{N48K}$ mutation in live larvae.

As indicated earlier, a marginal amount of hCLRN1$^{N48K}$ reaches the bundle in the larvae. The molecular mechanism associated with this trafficking is unknown. The canonical or conventional trafficking of wild-type hCLRN1 to the plasma membrane and hair bundle is dependent on the N-glycosylation and the PDZ domain binding sequence-type I (PDB) in its c-terminal. In general, N-glycosylation of membrane proteins is critical for their proper folding, coassembly and subsequent matriculation through the secretory pathway and loss of N-glycosylation in the membrane proteins is reported to result in its mislocalization in the ER. Accumulation of unfolded or misfolded proteins in the ER induces ERAD in addition to the ER stress signals due to unfolded protein response (UPR) involved in the unconventional trafficking of ER retained proteins. The UPR induced ER stress signals trigger phosphorylation of Golgi reassembly stacking protein 55 (hGRASP55)—a PDZ type I domain containing protein, and localization to the ER, where it mediates the selective Golgi bypassed unconventional secretion of ER retained cargos of misfolded N-glycoproteins with PDB type I sequence (S/T-X-Φ, 'X' can be any amino acid and 'Φ' can be hydrophobic amino acid, usually V, I or L) like ΔF508 mutant Cystic fibrosis transmembrane conductance regulator protein, ΔF508-CFTR. An alternative pathway to the hGRASP55 dependent unconventional secretion of PDB type-I cargo proteins is the Sorting nexin 27 (hSNX27) dependent PDZ domain type-I directed trafficking of PDB type I cargo proteins from the endosomes to the plasma membrane. Human CLRN1 being an N-glycoprotein with PDB type I sequence, we expect under UPR induced ER stress, either hGRASP55 or hSNX27 might unconventionally traffic hCLRN1$^{N48K}$ to the plasma membrane and hair bundle.

The retention of misfolded membrane proteins in the ER depends on its interactions with Ca$^{2+}$ dependent ER resident chaperone proteins. Thapsigargin (TG), a well-known UPR-inducing agent perturbs ER function by blocking the ER-Sarco/Endoplasmic Reticulum Ca$^{2+}$-ATPase (SERCA) pump and depleting ER luminal Ca$^{2+}$ stores. This action of TG activates hGRASP55 dependent unconventional secretory pathway through up-regulation of inositol-requiring protein 1α (IRE1α) induced MEK/ERK signaling pathway that phosphorylates hGRASP55, which in turn mediates cell-surface trafficking of ER retained misfolded PDB type I cargo proteins. We therefore postulated that reducing ER Ca$^{2+}$ stores with SERCA pump blockers like TG (an anticancer drug) or Artemisinin (ART) (an antimalarial drug)—would enhance/induce liberation of hCLRN1$^{N48K}$ from the ER and unconventional trafficking of ER retained proteins to the plasma membrane/hair bundle, where hCLRN1$^{N48K}$ would be able to function and correct the hair cell defects. In this Example, we have tried both genetic and biochemical (drug induced) rescue approaches to induce/enhance unconventional trafficking of hCLRN1$^{N48K}$ mutant protein to the hair bundle in transgenic zebrafish expressing hCLRN1$^{N48K}$-YFP in hair cells. In the genetic approach, we expressed either hGRASP55 or hSNX27 in the hair cells of the transgenic zebrafish expressing hCLRN1$^{N48K}$-YFP in hair cells to determine whether transient expression of the unconventional secretory cargo alone can efficiently traffic the hCLRN1$^{N48K}$ to the plasma membrane/hair bundle. And for the biochemical approach drug induced unconventional protein secretion approach, we used known SERCA pump blockers like TG and ART to trigger ER stress signal induced unconventional secretion of the hCLRN1$^{N48K}$ to the hair bundle. Results from these experiments support that hypothesis that hCLRN1$^{N48K}$ is transported to the bundle via the unconventional secretory pathway.

In sum, we developed an animal model system using zebrafish transgenesis and gene targeting to directly examine the function of human clarin-1 protein (hCLRN1) in hair cells and the ability of the pathogenic variant, hCLRN1$^{N48K}$, to support clarin-1-mediated function in hair cells in a clarin-1 deficient background. We show hCLRN1, like its zebrafish and mouse counterpart, preserves hair bundle integrity and function. Further, our zebrafish system allowed for biochemical and genetic interrogation of the mechanistic hypothesis and demonstrate that the intrinsic function of clarin-1 is not compromised by the $^{N48K}$ mutation but reduced availability of the protein in the mechanosensory bundle is the likely cause of the progressive dysfunction in hCLRN1$^{N48K}$ subjects. Concomitantly, the model we developed served as an in vivo tool to repurpose drugs that could potentially mitigate human mutant protein phenotype in hair cells. The results described herein show that an antimalarial drug, can mitigate sensory deficit associated with hCLRN1$^{N48K}$ mutation.

Materials and Methods

Zebrafish

All experiments were conducted using the Tübingen (Tu) strain of zebrafish of either sex. The zebrafish lines with the following genotypes clrn1$^{+/+}$, clrn1+/cwr1003 denoted here as clrn1+/KO, clrn1cwr1003/cwr1003 denoted here as clrn1$^{KO/KO}$ Tg(pvalb9:Hsa.CLRN1-YFP)cwr1005Tg denoted here as hCLRN1-YFP; clrn1$^{+/+}$, 28 Tg(pvalb9:Hsa.CLRN1 $^{N48K}$-YFP)cwr1006Tg denoted here as hCLRN1$^{N48K}$-YFP; clrn1$^{+/+}$, were all from Kumar Alagramam's lab. And the zebrafish lines Tg(pvalb9:Hsa. CLRN1-YFP)cwr1005Tg; clrn1cwr1003/cwr1003 denoted here as hCLRN1-YFP; clrn1$^{KO/KO}$, and Tg(pvalb9:Hsa. CLRN1 $^{N48K}$-YFP)cwr1006Tg; clrn1 cwr1003/cwr1003 denoted here as hCLRN1$^{N48K}$-YFP; clrn1$^{KO/KO}$ were generated in the current study by outcrossing the clrn1cwr1003/cwr1003 or clrn1$^{KO/KO}$ line with hCLRN1-YFP clrn1$^{+/+}$ and hCLRN1$^{N48K}$ YFP; clrn1$^{+/+}$ lines, respectively. The animal protocol used in this report were approved by the Case Western Reserve University Institutional Animal Care and Use Committee. All zebrafish were maintained and bred using standard procedures.

Generation of Clrn1$^{KO/KO}$ Zebrafish Line Transiently Expressing hCLRN1-YFP in the Hair Cells The protocol described previously was used to generate clrn1$^{KO/KO}$ zebrafish line that transiently expresses the hCLRN1-YFP transgene in the hair cells. Transgene construct Tg(pvalb9:Hsa. CLRN1-YFP) was generated as described earlier [Gopal et al., 2015; the new nomenclature for Parvalbumin-3b (pvalb3b) is pvalb9]. The Tg(pvalb9:Hsa. CLRN1-YFP) plasmid, along with Tol2 RNA, was injected into clrn1$^{KO/KO}$ zebrafish embryos at the single-cell stage. The advantage of this experiment is that the hair cell specific expression of Tg(pvalb9:Hsa. CLRN1-YFP) construct in mosaic pattern among hair cells of inner ear end-organ and neuromast in the injected larvae, gives an opportunity to analyze the difference in the hair bundle structure of hCLRN1-YFP; clrn1$^{KO/KO}$ hair cells in comparison to its adjacent clrn1$^{KO/KO}$ hair cells in an inner ear end-organ at the same plain of z-stack confocal images. Transgene expression was analyzed in live larvae at 6 day post fertilization (dpf) using an inverted Leica SP8 confocal microscope equipped with a 63× oil lens. All the Tg(pvalb9:Hsa. CLRN1-YFP) construct injected clrn1$^{KO/KO}$ larvae were anesthetized using MS-222 (Sigma-Aldrich) before screening for YFP to track the expression pattern of hCLRN1 tagged to YFP in the hair cells. Larvae expressing hCLRN1-YFP in their hair cells were identified by screening for YFP expressing hair cells in the injected larvae using fluorescence stereomicroscope (Leica MZFLIII). Then to compare the difference in the hair bundle structure of hCLRN1-YFP expressing clrn1$^{KO/KO}$ hair cell to its adjacent hCLRN1-YFP negative, clrn1$^{KO/KO}$ hair cell, z-stacks of single plain images of the inner ear organs under YFP channel (for hCLRN1-YFP expression) and DIC channel (to check the hair cell bundle structure) were imaged in parallel using confocal microscopy. The clrn1$^{KO/KO}$ hair cells were earlier reported to show splayed hair bundle phenotype compared to the intact cone shaped hair bundle structure observed in the wild-type Tü larvae. If the function of clarin-1 gene is conserved across species than we expect the expression of hCLRN1 in the clrn1$^{KO/KO}$ hair cell is capable of rescuing mutant splayed hair bundle phenotype and hair cell function.

Generation of Clrn1$^{KO/KO}$ Zebrafish Lines Stably Expressing hCLRN1-YFP or hCLRN1$^{N48K}$-YFP in the Hair Cells To generate the transgenic lines stably expressing either hCLRN1-YFP or pathogenic hCLRN1$^{N48K}$-YFP in the clrn1$^{KO/KO}$ zebrafish background, i.e., hCLRN1-YFP; clrn1$^{KO/KO}$ and hCLRN1$^{N48K}$-YFP; clrn1$^{KO/KO}$ zebrafishes, we outcrossed the clrn1$^{KO/KO}$ zebrafish with hCLRN1-YFP; clrn1$^{+/+}$, and hCLRN1$^{N48K}$-YFP; clrn1$^{+/+}$ zebrafish lines reported earlier. These 30 outcrosses resulted in the F1 generation of genotypes, hCLRN1-YFP; clrn1$^{+/KO}$ and hCLRN1$^{N48K}$-YFP; clrn1$^{+/KO}$, respectively. Further, the F1 generation fish carrying above mentioned genotypes were inbred to obtain F2 generation of required genotypes, hCLRN1-YFP; clrn1$^{KO/KO}$ and hCLRN1$^{N48K}$-YFP; clrn1$^{KO/KO}$. Screening for YFP expression in the larvae from F1 and F2 generation of hCLRN1-YFP; clrn1$^{KO/KO}$ and hCLRN1$^{N48K}$-YFP; clrn1$^{KO/KO}$ zebrafish lines, and genotyping to confirm the presence of clrn1$^{KO}$ allele either in homozygous or heterozygous state in the YFP positive larvae from both the hCLRN1-YFP; clrn1$^{KO/KO}$ and hCLRN1$^{N48K}$-YFP; clrn1$^{KO/KO}$ lines were carried out as described earlier. The F3 generation larvae from the hCLRN1-YFP; clrn1$^{KO/KO}$ and hCLRN1$^{N48K}$-YFP; clrn1$^{KO/KO}$ stable lines were used to study the changes in the clrn1$^{KO/KO}$ hair bundle phenotype associated with the presence of hCLRN1-YFP or pathogenic hCLRN1$^{N48K}$-YFP in live larvae at 6 dpf, using confocal microscopy (63× oil lens). At 6 dpf, larvae from hCLRN1-YFP; clrn1$^{KO/KO}$ and hCLRN1$^{N48K}$-YFP; clrn1$^{KO/KO}$ stable lines were anesthetized using MS-222 (Sigma-Aldrich) before screening for YFP expression in the hair cells. To compare the difference in the hair bundle structure of hCLRN1$^{N48K}$-YFP; clrn1$^{KO/KO}$ hair cells with the hCLRN1-YFP, clrn1$^{KO/KO}$ hair cells, z-stacks images of the inner ear organs from the hCLRN1-YFP; clrn1$^{KO/KO}$ and hCLRN1$^{N48K}$-YFP; clrn1$^{KO/KO}$ stable lines were captured under YFP channel (to confirm expression of hCLRN1-YFP or hCLRN1$^{N48K}$-YFP in the hair cells) and DIC channel (to check the hair cell bundle structure corresponding to genotype), using an inverted Leica SP8 confocal microscope equipped with a 63× oil lens objective. The clrn1$^{KO/KO}$ hair cells were earlier reported to show splayed hair bundle phenotype that affects mechanotransduction of hair cells compared to the intact cone shaped hair bundle 31 structure observed in the wild-type Tü larvae. If the function of clarin-1 gene is conserved across species than we expect the expression of hCLRN1 in the clrn1$^{KO/KO}$ hair cell should be capable of rescuing zebrafish clrn1$^{KO/KO}$ splayed hair bundle phenotype and have normal mechanotransduction. And in the hCLRN1$^{N48K}$YFP; clrn1$^{KO/KO}$ larvae, we expect progressive loss of hair cell function similar to that reported in USH3 individuals.

The startle response and swimming behavior of the clrn1$^{+/+}$ larvae, clrn1$^{KO/KO}$ larvae, hCLRN1-YFP; clrn1$^{KO/KO}$ larvae and hCLRN1$^{N48K}$-YFP; clrn1$^{KO/KO}$ larvae were recorded at 6.5 dpf, 10.5 dpf, 16.5 dpf and 27 dpf as described earlier (Table-1). The extracellular microphonics potentials were recorded at 6 dpf to confirm the hair cell function in these humanized zebrafish models for hCLRN1 (hCLRN1-YFP; clrn1$^{KO/KO}$ larvae) and USH3-CLRN1$^{N48K}$ mutant (hCLRN1$^{N48K}$-YFP; clrn1$^{KO/KO}$ larvae) as described earlier (FIG. 5).

bundle. To quantify the YFP fluorescence intensity, unadjusted 1 micron middle section images of four hair bundles per neuromast were analyzed in Image J. Fluorescence

TABLE 1

Survival rate and swimming/balance behavior of zebrafish from hCLRN1-YFP; clrn1$^{KO/KO}$ and hCLRN1$^{N48K}$-YFP; clrn1$^{KO/KO}$ stable lines

| Genotype | Survival rate | | | | | % showing startle response at 6.5 dpf | % of abnormal swimming-balance (6.5 dpf) | % of normal swimming-balance (>25 dpf) |
| --- | --- | --- | --- | --- | --- | --- | --- | --- |
|  | 6.5 dpf | 10.5 dpf | 15 dpf | 16.5 dpf | 27 dpf |  |  |  |
| clrn1$^{+/+}$ | 40 (100%) | 40 (100%) | 40 (100%) | 40 (100%) | 40 (100%) | 100 | 0 | 100 |
| clrn1$^{KO/KO}$ | 40 (100%) | 0 (0%) | N/A | N/A | N/A | 15 | 85 | N/A |
| hCLRN1-YFP; clrn1$^{KO/KO}$ | 40 (100%) | 40 (100%) | 40 (100%) | 40 (100%) | 40 (100%) | 100 | 0 | 100 |
| hCLRN1$^{N48K}$-YFP; clrn1$^{KO/KO}$ | 40 (100%) | 28 (70%) | 15 (37.5%) | 13 (32.5%) | 2 (5%) | 100 | 40 | 5* |
| Regimen I: hCLRN1$^{N48K}$-YFP; clrn1$^{KO/KO}$ treated with 0.4 µM ART from 3 to 7 dpf | 35 (100%) | 30 (85.71%) | 24 (68.57%) | 19 (54.29%) | 14 (40%) | 100 | 25.71 | 40 |
| Regimen II: hCLRN1$^{N48K}$-YFP; clrn1$^{KO/KO}$ treated with 0.4 µM ART from 3 to 12 dpf | 20 (100%) | 18 (90%) | 13 (65%) | 13 (65%) | 9 (45%) | # | # | 45 |

*Only 5% of hCLRN1$^{N48K}$-YFP; clrn1$^{KO/KO}$ larvae that show startle response survive to adult.
Till 7 dpf, Regimen I and II are similar in the treatment dosage, daily drug exposure time and clutch mates, so it is expected at 6.5 dpf the percentage of responders and abnormal swimmers will be same. So Regimen II larvae were not tested for startle response and swimming behavior at 6.5 dpf.

Transient Expression of Unconventional Secretory Pathway Carrier Proteins in the hCLRN1$^{N48K}$-YFP; Clrn1$^{+/+}$ Larvae Hair Cell The cDNAs encoding human Golgi reassembly stacking protein 55 (hGRASP55; NCBI accession number: NM_015530.3) and human Sorting Nexin Family member 27 (hSNX27; NCBI Accession number: NM_030918.5) were amplified from human retina RNA (Clontech Laboratories, Inc., USA) using infusion primer pairs, F1: 5'-GGCAGATCCACCATGatgggctcctcgcaaagcgtc-3' (SEQ ID NO: 1) and R1: 5'-CTAGTCAGTCACTAGttaaggtgactcagaagcat-3' (SEQ ID NO: 2) for hGRASP55, and F2: 5'-GGCAGATC-CACCATgatggcggacgaggacgggga-3' (SEQ ID NO: 3) and R2: 5'-CTAGTCAGTCACTAgctaatattcctctttctccac-3' (SEQ ID NO: 4) for hSNX27, respectively. The amplicon were sub-cloned into the pT3TS vector digested with NcoI and SpeI (InFusion Cloning Kit; Clontech Laboratories, Inc., USA) to generate pT3TS/hGRASP55 and pT3TS/hSNX27 constructs. Both, hGRASP55 and hSNX27 mRNA were synthesized from the XbaI linearized pT3TS/hGRASP55 and pT3TS/hSNX27 constructs using mMESSAGE mMACHINE T3 kit (Ambion, USA). Quality of the synthesized hGRASP55 and hSNX27 mRNA were analyzed using Agilent 2100 Bioanalyzer. Either hGRASP55 or hSNX27 mRNA was injected into the single cell stage hCLRN1$^{N48K}$-YFP; clrn1$^{+/+}$ embryos. At 4 dpf, hGRASP55 or hSNX27 mRNA injected hCLRN1$^{N48K}$-YFP; clrn1$^{+/+}$ larvae were examined for the change in the localization pattern of hCLRN1$^{N48K}$-YFP in the hair cells and bundle.

hCLRN1-YFP predominantly localize to the hair bundle and a weak expression in the hair cell membrane in the transgenic hCLRN1-YFP; clrn1$^{+/+}$ zebrafish line, and the human pathogenic variant hCLRN1$^{N48K}$-YFP mislocalized in the endoplasmic reticulum (ER) with a small amount manages to get trafficked to the hair bundle of the transgenic hCLRN1$^{N48K}$-YFP; clrn1$^{+/+}$ zebrafish larvae. A relative quantification of YFP fluorescence intensity was carried-out to compare the quantity of hCLRN1$^{N48K}$-YFP that manages to localize in the hair bundle to the hCLRN1-YFP in the hair bundle. To quantify the YFP fluorescence intensity, unadjusted 1 micron middle section images of four hair bundles per neuromast were analyzed in Image J. Fluorescence intensity is reported as the background subtracted Integrated Density value. While Confocal microscopy imaging of neuromast hair bundles from the above mentioned groups, YFP fluorescence channel was unadjusted between siblings from the tested groups, and images chosen for figures were near the mean of the group data. Z-stack image of neuromast hair cells were captures using SP2 confocal microscope and the YFP fluorescence measurements in the hair bundles from 1) control uninjected and 2) unconventional secretory pathway cargo injected groups were obtained using ImageJ. A triangle shaped region of interest covering the area of hair bundle in 1 micron thickness middle section of z-stack image of neuromast hair cells was used to obtain YFP fluorescence pixel intensity measurements (Ihair bundle) and an area without hair cells (Ibackground) in the same image. Fluorescence intensity of YFP (Iload) for each hair bundle in a given neuromast was normalized (Iload=Ihair bundle–Ibackground). We analyzed 4 hair bundle per neuromast per larva, and the YFP fluorescence intensity per neuromast was represented as average of 4 hair bundle YFP intensity (IAvg. load=Sum of Iload from 4 bundles in a neuromast/larva). And the mean of the total IAvg. load per group was considered for statistical comparison between groups. Student's t-test was used to confirm the observed changes in the YFP intensity in the hair bundles of hGRASP55 mRNA injected compared to hSNX27 mRNA injected and uninjected is significant.

Figure 4A:
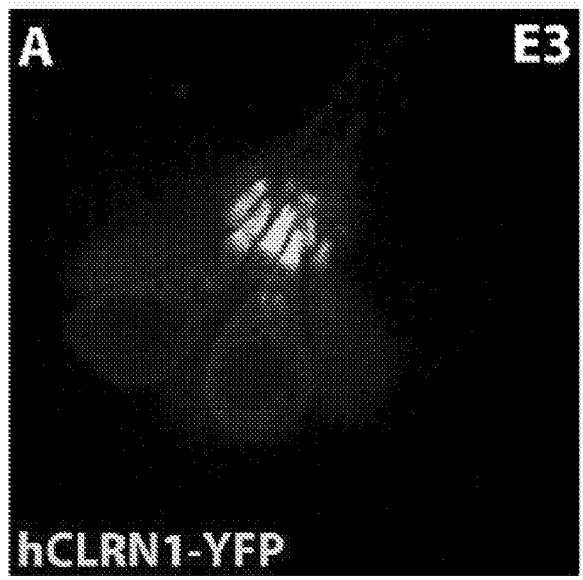
FIGS. 4(A-J) illustrate images and graphs showing SERCA inhibitors TG and ART are potent rectifiers of hCLRN1$^{N48K}$ mutant protein phenotype. SERCA inhibitor induced release of hCLRN1$^{N48K}$ retained in ER and enhanced trafficking of the mutant protein to the hair bundle is patent. SERCA inhibitors do not affect localization of the wild-type hCLRN1 protein in hair cells. (A-D) Neuromast hair cells from hCLRN1-YFP stable expressing larvae, (E-H) Neuromast hair cells from hCLRN1$^{N48K}$-YFP stable expressing larvae at 4 dpf. (A and E) E3 medium. (B and F) treated with 0.01% DMSO in E3 medium. (C and G) treated with 1 μM TG+0.01% DMSO in E3 medium. (D and H) treated with 0.4 μM ART+0.01% DMSO in E3 medium. Magnification, 40×. (I) Graph depicting the efficiency of the SERCA blocker drugs in rescuing the mutant protein to the hair cell bundle. Hair cells of 20 otic (O) and 20 middle (ML) neuromasts from 20 larvae in each group was considered for statistical analysis. Data represented as percentage of number of hair cells expressing the mutant protein in hair cell bundle divided by total number of hair cells considered for analysis. Mean±SEM; p value<0.0001. Images shown panels A-H were captured from live larvae. (J) Quantification of YFP intensity in the bundle using image J software. ****p value<0.0001, #ns=not significant.
Figure 4B:
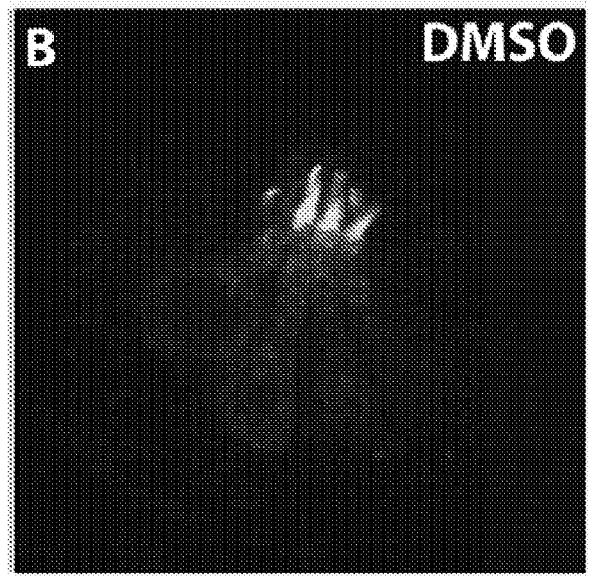
Figure 4C:
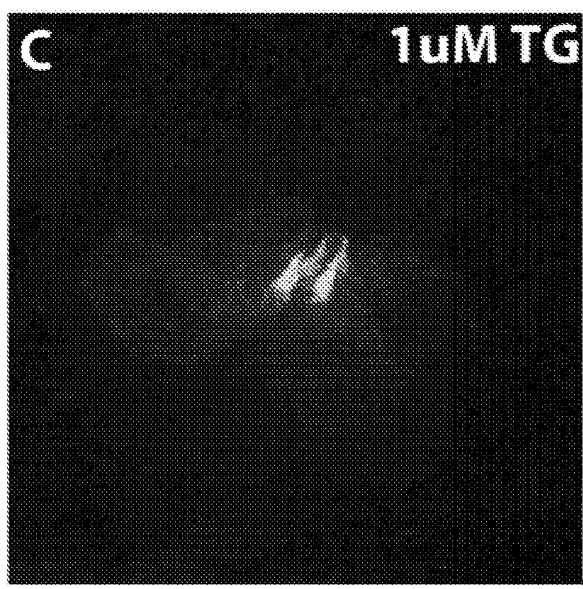
Figure 4D:
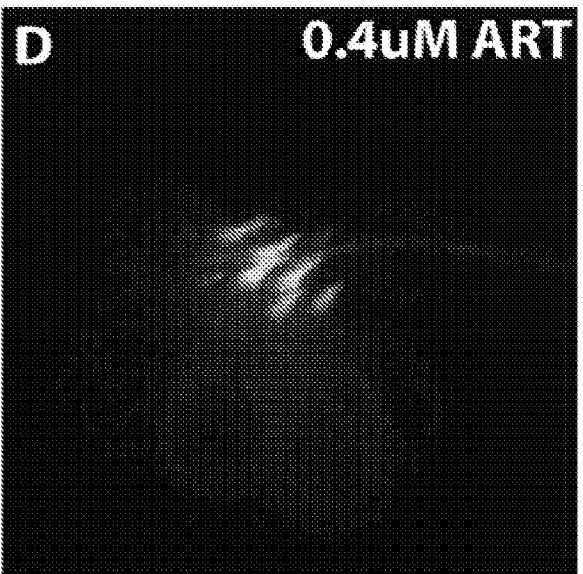
Figure 4E:
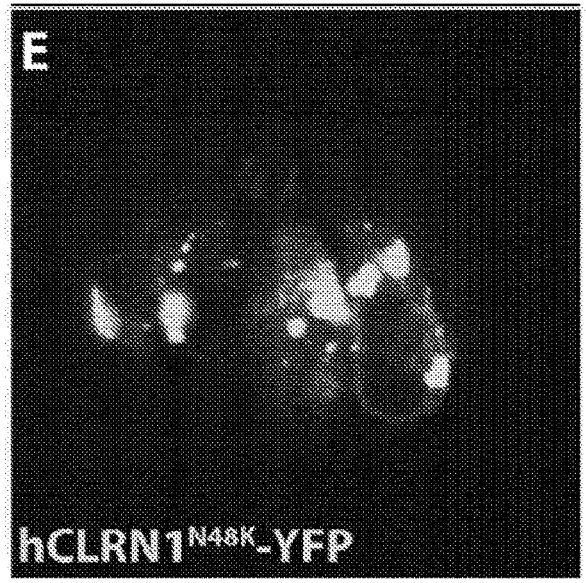
Figure 4F:
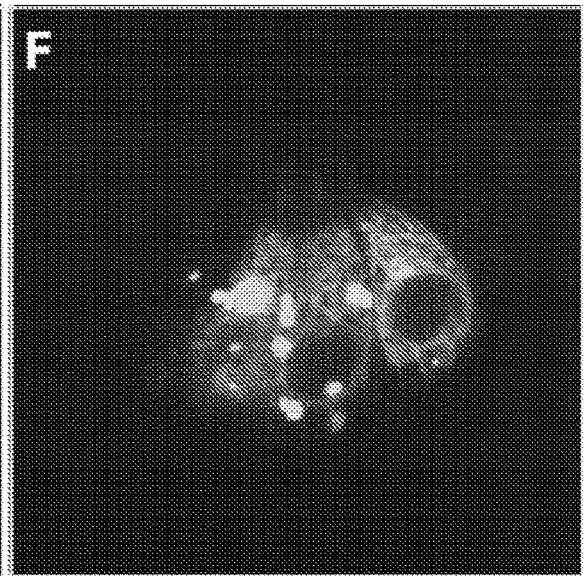
Figure 4G:
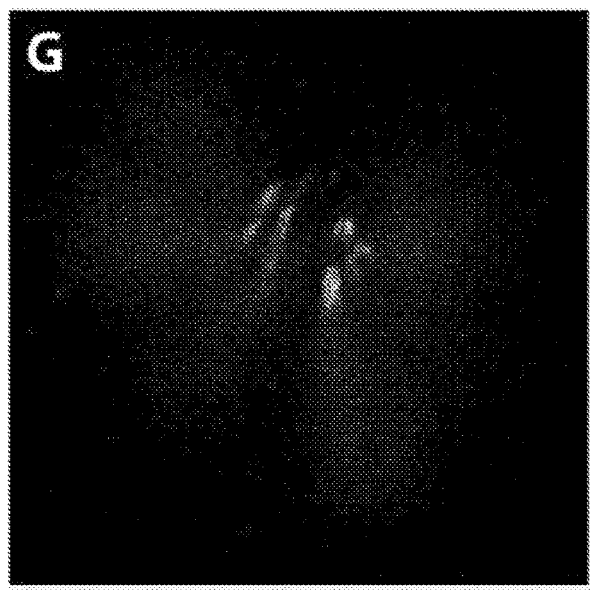
Figure 4H:
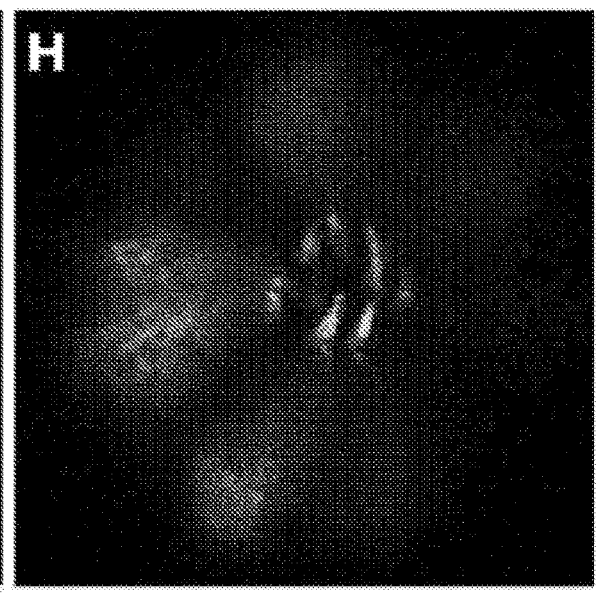

Treatment Regimen to Enhance the Hair Bundle Localization of Mutant hCLRN1$^{N48K}$YFP Protein Using SERCA Channel Inhibitor Drugs: Thapsigargin and Arthemisinin Thapsigargin (TG, 1 mg, Sigma-Aldrich, #T9033) stock in 100% DMSO was diluted in E3 medium to make the required final concentration of the drug. Five different concentrations that were earlier reported to induce ER stress and are non-toxic or lower lethal dose (LD50) in the zebrafish (0.1, 0.5, 1.0, 2.5, 5 µM concentrations) were used in this study. A total of 25 larvae per dosage and treatment duration from the genotypes hCLRN1$^{N48K}$-YFP; clrn1$^{+/+}$ and hCLRN1-YFP; clrn1$^{+/+}$, no older than 72 hours post fertilization (hpf) at the start of the experiment, were placed in a well of 12-well uncoated culture plate (BD Falcon, Canaan, Conn.). For ER stress induction, larvae were incubated in different dosage of TG from 1 hr to overnight at 28.5° C., followed by three times wash with E3 medium at 28.5° C. (Table. 2) and hair cells from the hCLRN1$^{N48K}$-YFP; clrn1$^{+/+}$ and hCLRN1-YFP; clrn1$^{+/+}$ lines were examined for the respective protein distribution pattern in the hair cell bundle and the cell body. Live confocal images of 'O' and 'ML1' neuromasts per larvae were capture using Leica SP2 confocal microscope with 40× oil immersion objective. Unadjusted 1 micron middle section images of four hair bundles per ML1 neuromast of larvae from TG treated and untreated groups were analyzed using Image J software version v. 1.48 (FIG. 4). The hair bundle trafficked amount of hCLRN1$^{N48K}$ protein corresponds to the change in YFP intensity in the hair bundle in the TG treated larvae. Quantification of YFP fluorescence intensity was carried out as described in the previous experiment for unconventional trafficking of hCLRN1$^{N48K}$-YFP by hGRASP55 cargos. The maximum level of hCLRN1$^{N48K}$-YFP trafficked to hair bundle was observed in hCLRN1$^{N48K}$-YFP; clrn1$^{+/+}$ larvae exposed for 4 hours in 1 uM TG dosage group. Student's t-test was used to confirm the observed changes in the YFP intensity in the hair bundles of TG treatment compared to untreated hCLRN1$^{N48K}$-YFP; clrn1$^{+/+}$ larvae, is significant (FIG. 4J).

TABLE 2

TG drug dose and treatment duration used to treat the hCLRN1$^{N48K}$-YFP; clrn1$^{+/+}$ larvae to induce unconventional protein secretion

| TG Dose (μM) | Exposure time (in hours) | | | | | |
|---|---|---|---|---|---|---|
| | 1 | 2 | 3 | 4 | 8 | 16 |
| 0.1 | S | S | S | S | S | S |
| | — | — | — | — | — | — |
| 0.5 | S | S | S | S | S | L |
| | — | — | — | — | — | ND |
| 1.0 | S | S | S | S | L | L |
| | — | — | + | ++ | ND | ND |
| 2.5 | L | L | L | L | L | L |
| | ND | ND | ND | ND | ND | ND |
| 5.0 | L | L | L | L | L | L |
| | ND | ND | ND | ND | ND | ND |

'S' = Surviving;
'L' = Lethal;
'ND' = Not determined
"—" = The YFP intensity in the bundle is similar to untreated control.
"+" = The YFP intensity in the bundle is higher compared to untreated control.

Arthemisinin (ART, 100 mg, Sigma-Aldrich, #361593) in 100% DMSO was diluted in E3 medium to make the final concentration. Five different concentrations within the range of reported ER stress inducing level in the zebrafish (0.1, 0.25, 0.4, 0.5, and 1 μM concentrations) were used in this study. A total of 25 larvae, no older than 72 hpf at the start of the experiment, were placed in a well of 12-well uncoated culture plate (BD 35 Falcon, Canaan, Conn.). For ER stress induction, larvae were exposed in different dosage of ART for different duration at 28.5° C. (Table 3) and washed three times with E3 medium, and hair cells from the hCLRN1-YFP; clrn1$^{+/+}$ larvae and hCLRN1$^{N48K}$-YFP; clrn1$^{+/+}$ larvae were examined for the respective protein distribution pattern in the hair cell bundle and the cell body. Live confocal Z-stack images of otic 'O' and middle 'ML' neuromasts per larvae of hCLRN1-YFP; clrn1$^{+/+}$ larvae and hCLRN1$^{N48K}$-YFP; clrn1$^{+/+}$ genotypes from the untreated group in the E3 medium, 0.01% DMSO treatment group and ART treatment group were capture using Leica SP2 confocal microscope at 40× oil immersion objective. Hair cells from 2 otic (0) and 2 middle (ML) neuromasts per larvae were examined for the change in YFP intensity in the hair bundle and cell body. From the captured confocal images of these neuromast hair cells, unadjusted 1 micron middle section images of 4 mature hair bundles from ML1 neuromast per larvae were considered for the YFP intensity quantification in unadjusted ROI covering the middle section of each hair bundles using the imageJ software. The maximum level of hCLRN1$^{N48K}$-YFP trafficked to hair bundle was observed in hCLRN1$^{N48K}$-YFP; clrn1$^{+/+}$ larvae exposed for 4 hours in 0.4 uM ART dosage group. The hair bundle trafficked amount of hCLRN1$^{N48K}$ protein corresponds to the change in YFP intensity in the hair bundle in the ART treated larvae. Quantification of YFP fluorescence intensity was carried out as described in the previous experiment for unconventional trafficking of hCLRN1$^{N48K}$-YFP by hGRASP55 cargos. Student's t-test was used to confirm the observed changes in the YFP intensity in the hair bundles of ART treatment compared to untreated and TG treated hCLRN1$^{N48K}$-YFP; clrn1$^{+/+}$ larvae, is significant (FIG. 4J).

TABLE 3

ART drug dose and treatment duration used to treat the hCLRN1$^{N48K}$-YFP; clrn1$^{+/+}$ larvae to induce unconventional protein secretion

| ART Dose (μM) | Exposure time (in hours) | | | | | | Post-exposure hair cell body hCLRN1N48K aggregates recovery time in 4 hours 0.4 μM ART exposure group (in hours) | | |
|---|---|---|---|---|---|---|---|---|---|
| | 1 | 2 | 4 | 6 | 8 | 10 | 10 | 24 | 48 |
| 0.1 | S | S | S | S | S | S | S | S | S |
| | — | — | — | — | — | — | — | — | — |
| 0.25 | S | S | S | S | S | S | S | S | S |
| | — | — | — | — | — | — | — | — | — |
| 0.4 | S | S | S | S/L | L | L | S | S | S |
| | — | — | ++ | + | ND | ND | ++* | ++++* | ++++* |
| 0.5 | L | L | L | L | L | L | N/A | | |
| | ND | ND | ND | ND | ND | ND | | N/A | N/A |

TABLE 3-continued

ART drug dose and treatment duration used to treat the hCLRN1$^{N48K}$-YFP; clrn1$^{+/+}$ larvae to induce unconventional protein secretion

| ART Dose | Exposure time (in hours) | | | | | | Post-exposure hair cell body hCLRN1N48K aggregates recovery time in 4 hours 0.4 µM ART exposure group (in hours) | | |
|---|---|---|---|---|---|---|---|---|---|
| (µM) | 1 | 2 | 4 | 6 | 8 | 10 | 10 | 24 | 48 |
| 1.0 | L ND | L ND | L ND | L ND | L ND | L ND | N/A | N/A | N/A |

'S' = Surviving;
'L' = Lethal;
'S/L' Larvae surviving with apoptosis/necrosis of hair cells;
'ND' = Not determined
"—" = The YFP intensity in the bundle is similar to untreated control.
"+" = The YFP intensity in the bundle is higher compared to untreated control.
"*" = The YFP intensity of the hCLRN1N48K aggregates in the hair cell body from post ART treatment recovery groups.
N/A = At Lethal (L) dosage, post recovery is not applicable.

Figure 4I:
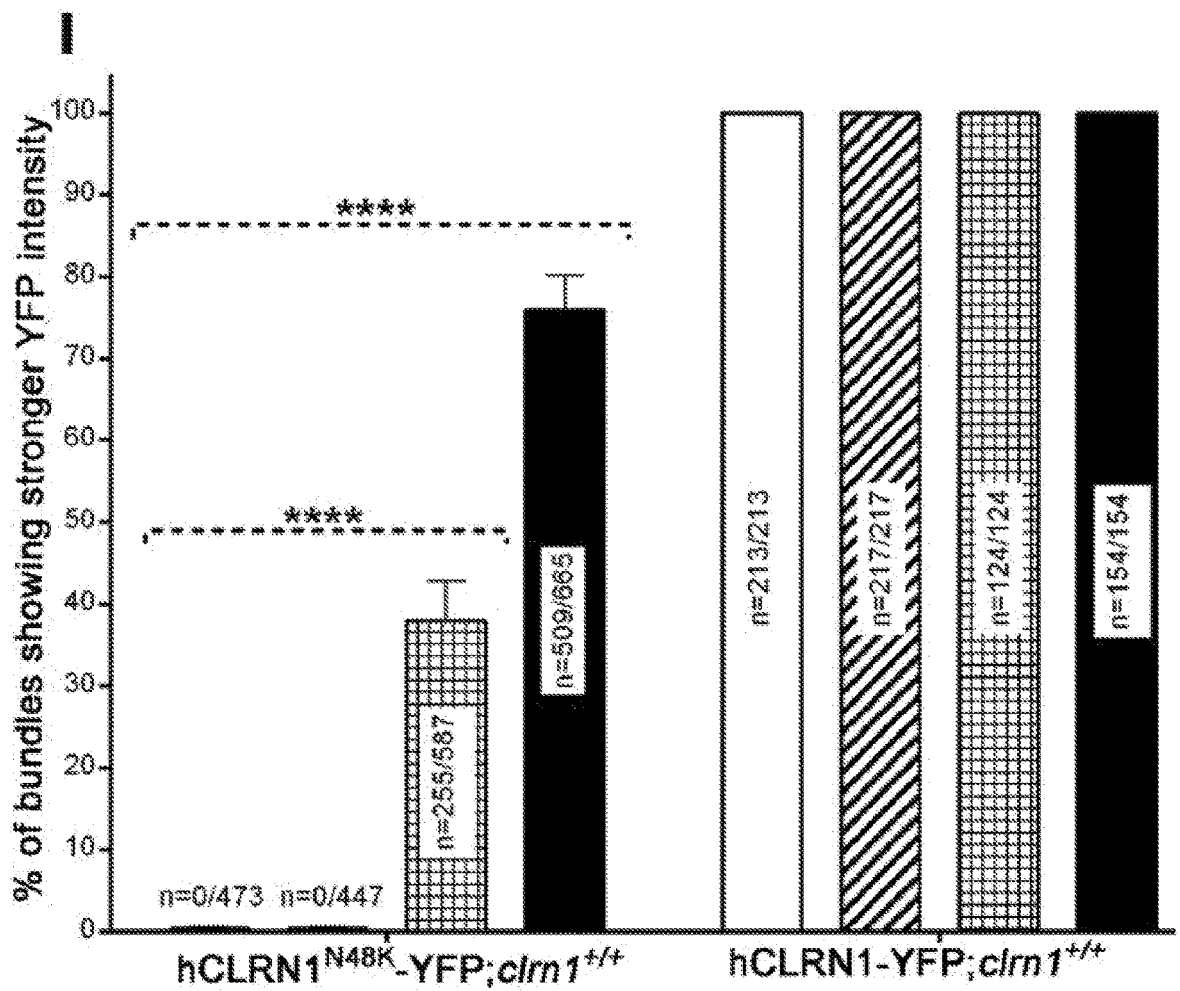
Figure 4J:
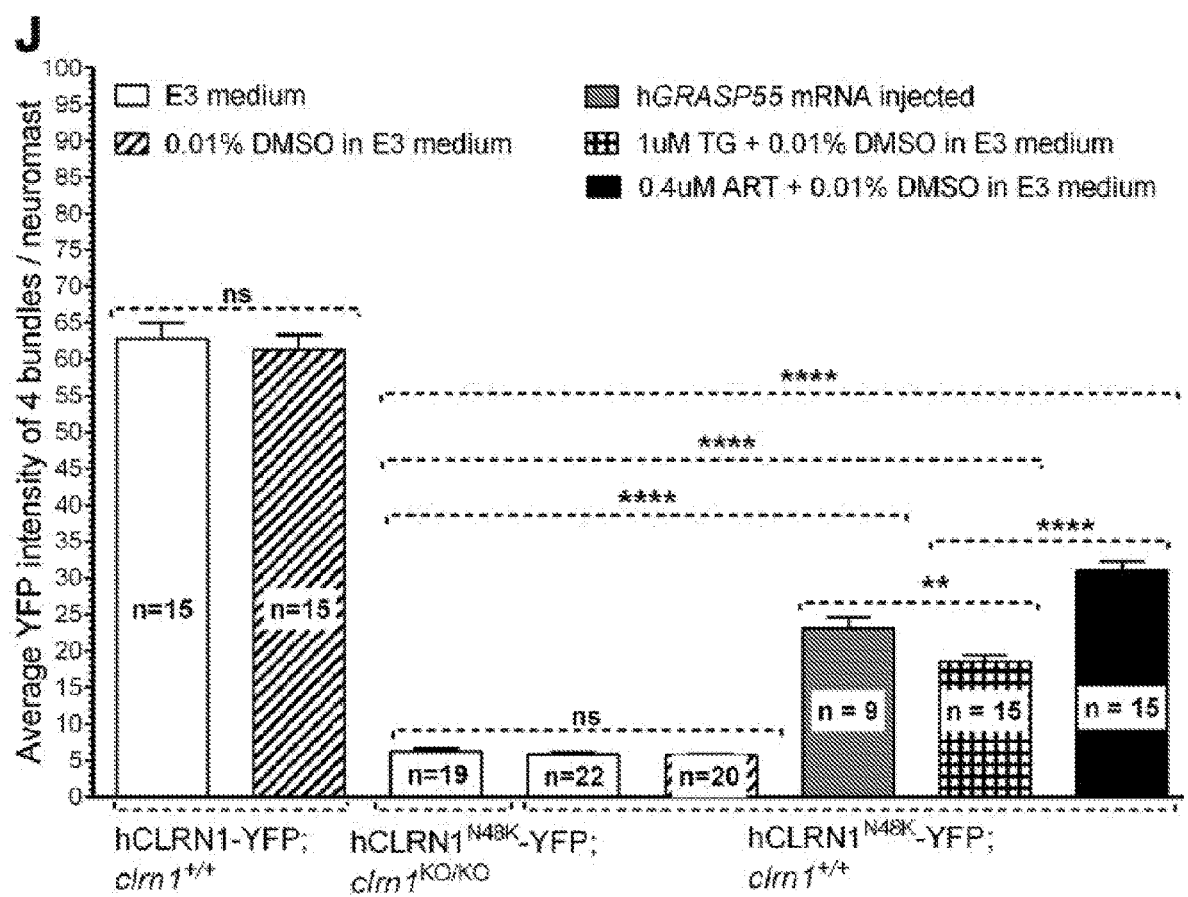

The bar graph for the TG or ART treated and untreated group from the hCLRN1-YFP; clrn1$^{+/+}$ larvae and hCLRN1$^{N48K}$-YFP; clrn1$^{+/+}$ larvae was drawn using the percentage of hair bundles expressing the YFP protein in the bundle of the corresponding neuromast hair cells in a group (FIG. 4I).

Recording Microphonic Potentials in Clrn1$^{KO/KO}$ Zebrafish with Hair Cell Specific Stable Expression of Either hCLRN1-YFP or hCLRN1$^{N48K}$-YFP, and ART Treated hCLRN1$^{N48K}$YFP;clrn1$^{KO/KO}$ Larvae Zebrafish larvae at 6 dpf were anesthetized using MS-222 (Sigma-Aldrich) dissolved in a standard bath solution containing 120 mM NaCl, 2 mM KCl, 10 mM HEPES, 2 mM CaCl2, and 0.7 mM NaH2PO4 adjusted to pH~7.2. The larvae were then secured in a recording chamber using dental floss tie downs (Ricci and Fettiplace, 1997). Their blood flow and heart rate were visually observed to assess viability using an upright Olympus BX51WI microscope. Recordings were made with a PC-505B amplifier (Warner Instruments) and a PCI-6221 digitizer (National Instruments). Images were taken with a Grasshopper3 CMOS camera (Point Grey) and processed with software provided by the manufacturer. To record the activity of hair cells from the lateral line neuromasts, the cupula of neuromasts were deflected with a fluid jet placed ~50 m from the neuromast (Trapani and Nicolson, 2010) and controlled by an HSPC-1 (ALA Scientific Instruments) that delivered sinusoidal stimuli of 50 Hz. Microphonic potentials were recorded at room temperature (22° C.). For this, borosilicate glass electrodes with a resistance of 5-6 MS were filled with standard bath solution and placed near the apical edges of the lateral line neuromasts. Microphonic potentials were recorded using a jClamp for Windows (SciSoft, license: Joseph Santos-Sacchi, Yale University, New Haven, Conn.) in current-clamp mode, amplified by 20 (SIM983; Stanford Research), and low-pass filtered at 200 Hz. The data represent an average of at least 500 responses. Statistical significance was set at $p<0.05$.

Results

Human Clarin-1 Protein Rescues Ear Phenotype in Clarin-1 Null Zebrafish

Zebrafish clarin-1 (Clrn1) and human clarin-1 (hCLRN1) proteins localize to the hair cell bundle ("hair bundle"), and disabling mutation in clarin-1 results in loss of hair bundle integrity and hair cell function in zebrafish and mouse models for USH3 syndrome. Amino acid sequence of clarin-1 in zebrafish is 61% identical to the human and 58% identical to the mouse. These data suggests hCLRN1 retains the same function as the zebrafish and mouse counterparts. If this hypothesis is true, hCLRN1 should be able to preserve hair bundle integrity and rescue loss of clarin-1 function in an animal model. To test this hypothesis, Tg(pvalb9: Has.CLRN1-YFP) construct with Tol2 RNA was injected into single-cell stage clrn1$^{KO/KO}$ embryos ($F_0$ generation), and hair cells were examined at 6 dpf [pvalb9 is a hair cell-specific promoter. One advantage of this approach is not all hair cells in the developing zebrafish clrn1$^{KO/KO}$ larvae will inherit the injected transgene, allowing comparison between transgenepositive and transgene-negative cells side-by-side in the same specimen (Larvae). The disadvantage, however, is the number of transgene-positive hair cells is small (<10 cells/inner ear sensory organ/6 dpf larvae) to translate to whole-organ function rescue. Consistent with expectation for an $F_0$ generation injection, only a small number (5-10 cells) of hair cells in the inner ear and/or lateral line displayed YFP-positive hair bundles, confirming expression and targeting of hCLRN1 in those hair cells (n=30, hCLRN1-YFP positive larvae were examined; FIGS. 1A and D). Importantly, all YFP positive cells showed wild-type hair bundle morphology whereas the hair bundles of the surrounding YFP-negative hair cells were splayed or disrupted (FIGS. 1A-F; Arrow—YFP positive hair cells displaying cone shaped clrn1$^{+/+}$ bundle morphology, Arrow head—YFP negative hair cells displaying splayed or disrupted hair bundle morphology). Results show that hCLRN1 rescued the hair bundle phenotype in clrn1$^{KO/KO}$ hair cell, proving that hCLRN1 can functionally substitute for zebrafish Clrn1 protein.

To confirm this result and to determine whether expression of hCLRN1 rescues hearing and balance function in clrn1$^{KO/KO}$ zebrafish, we generated clrn1$^{KO/KO}$ zebrafish stably expressing hCLRN1-YFP in hair cells (hCLRN1-YFP; clrn1$^{KO/KO}$) (FIGS. 1G-L). The clrn1$^{+/+}$ zebrafish larvae (6 dpf) display burst or slow swims, and the startle stimulus always induced a burst swim response. In contrast, clrn1$^{KO/KO}$ larvae (6 dpf) typically display shorter periods of spontaneous swim and often settle at the bottom. Following the startle stimulus, mutants swim in short spurts away from the bottom of the dish toward the surface and then quickly tumbled back to the bottom or fail to respond. The clrn1$^{KO/KO}$ larvae with normal swim bladders fail to maintain their body axis parallel to the surface and frequently sank to the bottom in a head-down position and slowly settled on their lateral side. The clrn1$^{KO/KO}$ larvae seldom survive beyond 15 dpf. We believe this is due to 'bottom dwelling' which reduces the ability of the larvae to feed and avoid suffocation from detritus.

Figure 5A:
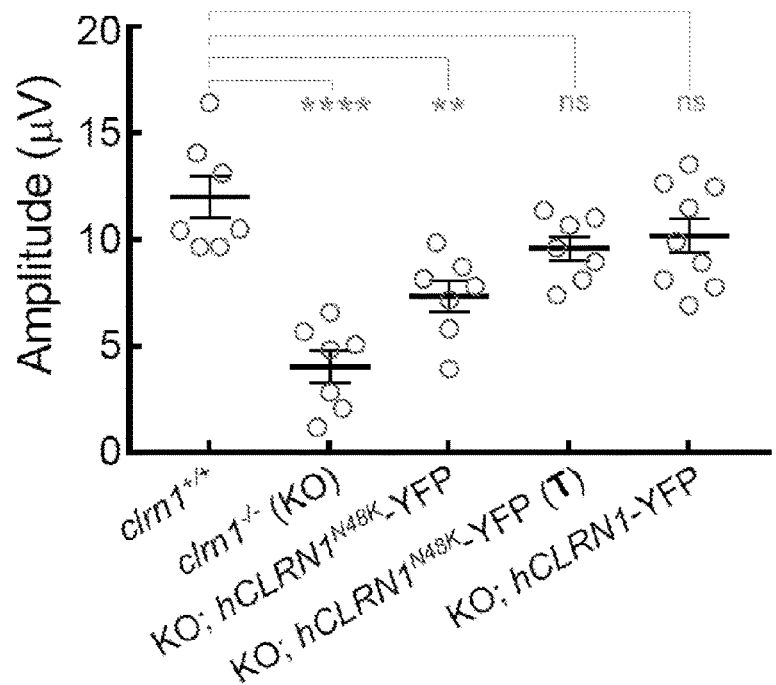
FIGS. 5(A-C) illustrate plots showing enhanced hair bundle trafficking of hCLRN1$^{N48K}$ through SERCA inhibitors activated GRASP55 cargo dependent unconventional protein secretory pathway improved microphonic potentials in the neuromasts of the clrn1$^{KO/KO}$ larvae. A, Summary of microphonic potential peak-to-peak amplitudes at twice the stimulus frequency. Average values of microphonic potentials obtained from lateral line neuromasts from 6 dpf zebrafish larvae of following genotypes, clrn1$^{+/+}$, clrn1$^{KO/KO}$ is (KO), KO; hCLRN1-YFP, KO; hCLRN1$^{N48K}$-YFP and 0.4 μM ART treated KO; hCLRN1$^{N48K}$—YFP group is KO; B, Number of hair cells per neuromast from clrn1$^{+/+}$, clrn1$^{KO/KO}$ KO), KO; hCLRN1-YFP, KO; hCLRN1$^{N48K}$ YFP and 0.4 μM ART treated KO; hCLRN1$^{N48K}$—YFP group is KO; hCLRN1$^{N48K}$-YFP (T) larvae. Data represent the mean±SEM. Analysis of the same larvae (n=7 in all groups except KO; hCLRN1-YFP, n=8) is shown in A and B. Asterisks indicate statistical significance and ns indicates non significance, one way ANOVA, 'ns' is p≥0.05, '' is p<0.01, and '**' is p<0.0001. C, Representative trace microphonic potentials recorded from KO; hCLRN1-YFP, KO; hCLRN1$^{N48K}$-YFP, 0.4 μM ART treated KO; hCLRN1$^{N48K}$ YFP (T) larvae and Stimulus (top trace) are shown here. The top trace shows pressure applied to the stimulating puff pipette.
Figure 5B:
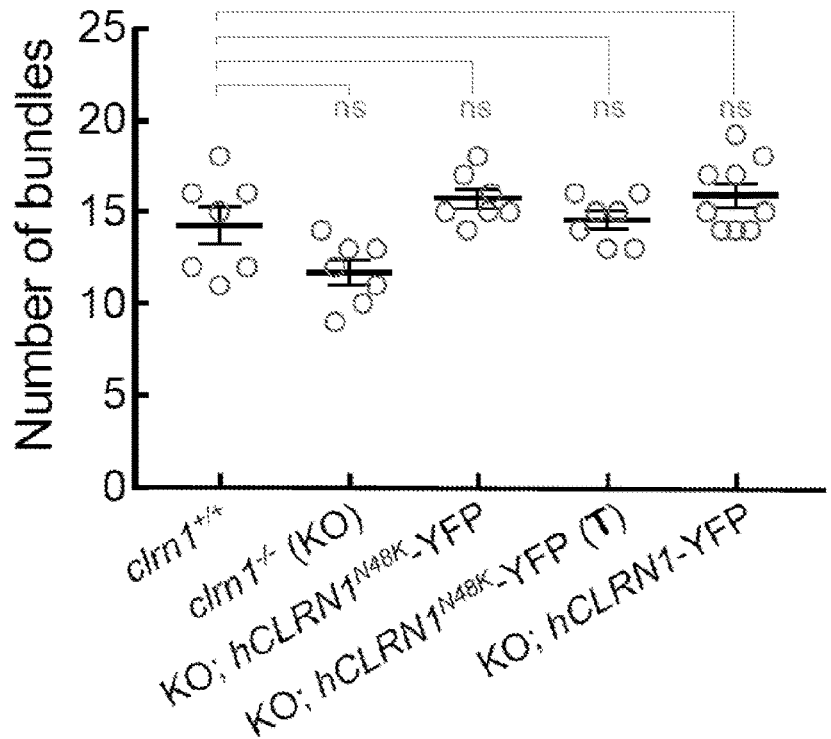
Figure 5C:
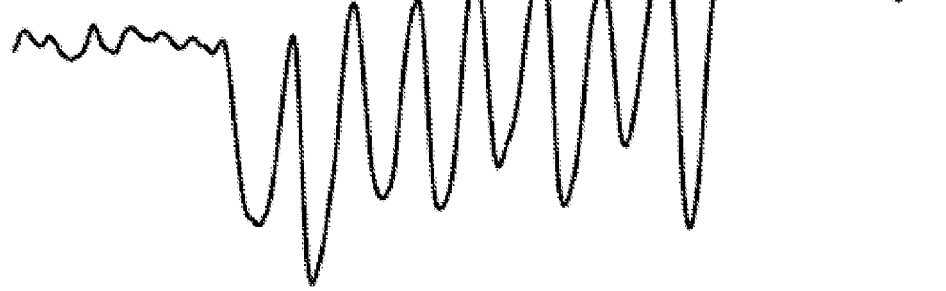
Figure 5C:
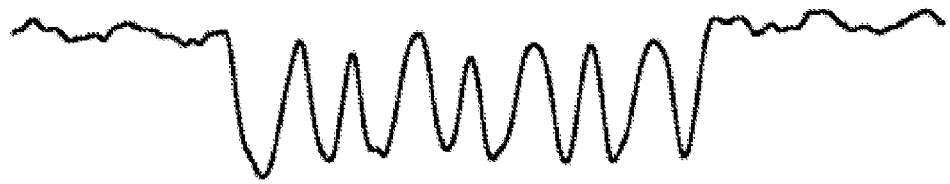

The hCLRN1-YFP; clrn1$^{KO/KO}$ larvae were indistinguishable from clrn1$^{+/+}$ controls with regard to survival, size, shape, and swimming behavior. Video footages of the swimming behavior of clrn1$^{KO/KO}$ larvae and hCLRN1-YFP; clrn1$^{KO/KO}$ larvae captures the dramatic difference and demonstrates rescue of the phenotype in the knockout line expressing hCLRN1-YFP. Examination of hair cells in the inner ear and lateral line neuromast from hCLRN1-YFP; clrn1$^{KO/KO}$ larvae (n=50) shows YFP positive bundles are comparable to wild-type (clrn1$^{+/+}$) hair bundles, indicating complete rescue of the hair bundle phenotype in clrn1$^{KO/KO}$ larvae (FIG. 1G-L). To check whether the preservation of normal hair bundle structure by substitution of hCLRN1-YFP in the hair cells of clrn1$^{KO/KO}$ zebrafish (hCLRN1-YFP; clrn1$^{KO/KO}$) improves its mechanotransduction, the extracellular microphonic potentials were recorded from hair cells of two lateral line neuromasts per larvae in response to fluid jet mechanostimulation from clrn1$^{+/+}$, clrn1$^{KO/KO}$, and hCLRN1-YFP; clrn1$^{KO/KO}$ zebrafish larvae at 6 dpf (FIGS. 5A-5C; n=7 from each group). As expected, we observed significant improvement in the extracellular microphonic potentials recorded from hCLRN1-YFP; clrn1$^{KO/KO}$ larvae compared to clrn1$^{KO/KO}$ mutants, and it was commensurate with the recording from hair cells of clrn1$^{+/+}$ larvae (FIGS. 5A, C). Recordings from the neuromast hair cells from clrn1$^{+/+}$, clrn1$^{KO/KO}$, and hCLRN1-YFP; clrn1$^{KO/KO}$ larvae revealed stimulus-evoked microphonic potentials of 11.93±0.98 µV, 3.96±0.76 µV, and 10.12±0.803 µV (mean±SEM; n=7; FIG. 5A-5C), respectively. 14 Observed difference in the recorded microphonic potential values of clrn1$^{KO/KO}$ and hCLRN1-YFP; clrn1$^{KO/KO}$ groups were statistically significant (p<0.001; student's t-test). No significant difference was found between the number of hair cells in the neuromasts of above mentioned all three groups (FIG. 5B), indicating that the attenuated microphonic potentials in the clrn1$^{KO/KO}$ is from defective function of hair cells and the significant increase in potentials of hCLRN1-YFP; clrn1$^{KO/KO}$ group is from improvement in function of hair cells, and not from difference in the hair cells count. Therefore, the significant improvement in microphonic potential recorded from hCLRN1-YFP supplemented hair cells of clrn1$^{KO/KO}$ larvae (hCLRN1-YFP; clrn1$^{KO/KO}$) could result from hCLRN1-YFP depended maintenance of normal cone shaped hair bundle structure in hair cells of clrn1$^{KO/KO}$ larvae.

The clrn1$^{KO/KO}$ larvae seldom survived beyond 15 dpf, in contrast, hCLRN1-YFP; clrn1$^{KO/KO}$ males and females survived as long as clrn1$^{+/+}$ controls, and were able to breed successfully, with the clutch size comparable to clrn1$^{+/+}$ parent in Tü strain background. These results support the hypothesis that A) hCLRN1 is a true ortholog of the zebrafish and mouse clarin-1 genes, B) shown that fusion of YFP to the C-terminus of hCLRN1 does not affect localization or function of the protein and C) bestow zebrafish as an in vivo model for the functional analysis of wild-type and pathogenic variants of hCLRN1.

Zebrafish Clrn1$^{KO/KO}$ Expressing Pathogenic Variant of Human Clarin-1 (hCLRN1$^{N48K}$) Protein Shows Variable, Progressive Loss of Hair Cell Function The N-glycosylation site mutation in hCLRN1 (hCLRN1$^{N48K}$) is one of the two most common causes of USH3 among the Ashkenazi Jewish origins. The hCLRN1$^{N48K}$ subjects develop hearing but progressively lose that function over time. Suggesting the function of hCLRN1 is not compromised by the $^{N48K}$ mutation rather reduced availability of the mutant protein in the hair bundle may be the cause of phenotype. If this assumption is true, and since hCLRN1 rescues hair cell phenotype in clrn1$^{KO/KO}$ zebrafish, we hypothesized that clrn1$^{KO/KO}$ zebrafish expressing hCLRN1$^{N48K}$ would develop ear function but fail to retain it. To determine if clrn1$^{KO/KO}$ zebrafish expressing hCLNR1$^{N48K}$ in the hair cells would display a progressive phenotype, we generated clrn1$^{KO/KO}$ zebrafish stably expressing hCLRN1$^{N48K}$-YFP in hair cells (hCLRN1$^{N48K}$-YFP; clrn1$^{KO/KO}$) (FIG. 2). As we reported in Gopal et al., 2015, a small portion of misfolding mutant protein hCLRN1$^{N48K}$YFP, managed to escape the ERAD degradation and expressed in the hair bundle in the early larval stage (6 dpf) as shown here in the FIG. 2. All the hCLRN1$^{N48K}$-YFP positive hair cells showed cone-shaped (wild-type) bundle morphology at 6 dpf (FIGS. 2C and 2F), confirming that the function of hCLRN1$^{N48K}$ protein is not compromised by the $^{N48K}$ mutation and if trafficked to its functional domain, can restore the hair bundle morphology in clrn1$^{KO/KO}$ zebrafish. At 6 dpf, mature hCLRN1$^{N48K}$-YFP positive clrn1$^{KO/KO}$ hair cells with cone-shaped hair bundles were tested for microphonic potentials to identify whether the presence of hCLRN1$^{N48K}$ in these hair cells helps to have normal mechanotransduction that is known to be attenuated in the absence of clarin-1 from earlier report on clrn1$^{KO/KO}$ null mutants. The extracellular microphonic potentials were recorded from hair cells of two neuromasts/larvae from seven hCLRN1$^{N48K}$-YFP; clrn1$^{KO/KO}$ zebrafish larvae (FIG. 5A-5C). The extracellular microphonic potentials recorded from hCLRN1$^{N48K}$-YFP; 16 clrn1$^{KO/KO}$ larvae (7.286±0.744 µV; Mean±SEM) show increase in potentials by nearly 2 folds compared to clrn1$^{KO/KO}$ mutants (3.966±0.76 µV; FIG. 5A), endorses the hair cell function improvement. In summary, the observed significant improvement in hair bundle structure and microphonic potentials concludes that hCLRN1$^{N48K}$-YFP supplemented the role of clarin1 in clrn1$^{KO/KO}$ hair cells of hCLRN1$^{N48K}$-YFP; clrn1$^{KO/KO}$ larvae, and also confirms that hCLRN1$^{N48K}$-YFP protein is functional. Though, the presence of hCLRN1$^{N48K}$-YFP in clrn1$^{KO/KO}$ mutants significantly improved the extracellular potentials in hair cells from hCLRN1$^{N48K}$-YFP; clrn1$^{KO/KO}$ larvae, it was not equivalent to extracellular potentials recorded from hCLRN1-YFP; clrn1$^{KO/KO}$ hair cells (10.12±0.76 µV; FIG. 5A). This could be due to the observed difference in the intensity/quantity of hCLRN1-YFP and hCLRN1$^{N48K}$-YFP localized to the hair bundle (FIGS. 1 and 2), resulting from defect in trafficking of misfolding mutant hCLRN1$^{N48K}$ protein to the bundle due to it been constantly degraded by the ERAD system.

At 6.5 dpf, clrn1$^{+/+}$ larvae often tend to swim towards the middle or closer to surface of the water (E3 medium) in the Petri dish, and escape swiftly from the field of view when startled (by tapping the Petri dish with a metal probe). At 6.5 dpf, hCLRN1$^{N48K}$-YFP; clrn1$^{KO/KO}$ larvae (n=40) were hard to distinguish from clrn1$^{+/+}$ larvae in a Petri dish when viewed from the top. Examination of hCLRN1$^{N48K}$-YFP; clrn1$^{KO/KO}$ larvae from the side of the Petri dish at 6.5 dpf revealed disabilities in some of the larvae. About 40% (n=16) showed subdued swimming behavior and attenuated startle response; they often tend to settle at the bottom of the Petri dish and move in 'short hops' and display incomplete escape in response to tapping; several taps are required to prod some larvae to move out of the field of view. To monitor hair cell function in the hCLRN1$^{N48K}$-YFP; clrn1$^{KO/KO}$ zebrafish, larvae from several clutch were observed longitudinally from 6.5 to 27 dpf for survival, swimming behavior and startle response (Table 1). Only a small percentage (5%; n=2) of hCLRN1$^{N48K}$-YFP; clrn1$^{KO/KO}$ larvae survived beyond 25 dpf, and the deteriorating swim behavior and startle response indicates that sensory function associated with hair cells deteriorates over time in majority of the hCLRN1$^{N48K}$-YFP; clrn1$^{KO/KO}$ zebrafish larvae (Table 1). However, ~5% of the hCLRN1$^{N48K}$-YFP; clrn1$^{KO/KO}$ zebrafish do survive long enough to be able to breed like its clrn1$^{+/+}$ counterpart. Overall, results show the hCLRN1$^{N48K}$-YFP; clrn1$^{KO/KO}$ zebrafish model display variable onset progressive loss of hair cell function. In this model, hair cells expressing hCLRN1$^{N48K}$ retained hair bundle structure and function for a longer duration than clrn1$^{KO/KO}$ hair cells, consistent with previous report 'USH3-CLRN1Y176X individuals develop severe hearing loss earlier in life compared with CLRN1$^{N48K}$ individuals'. This new model for inner ear disorder associated with hCLRN1$^{N48K}$ mutation will be useful to identify therapeutic agents to prevent progressive loss of hair cell function in USH3-CLRN1$^{N48K}$ mutant individuals.

Figures 3A, 3B:
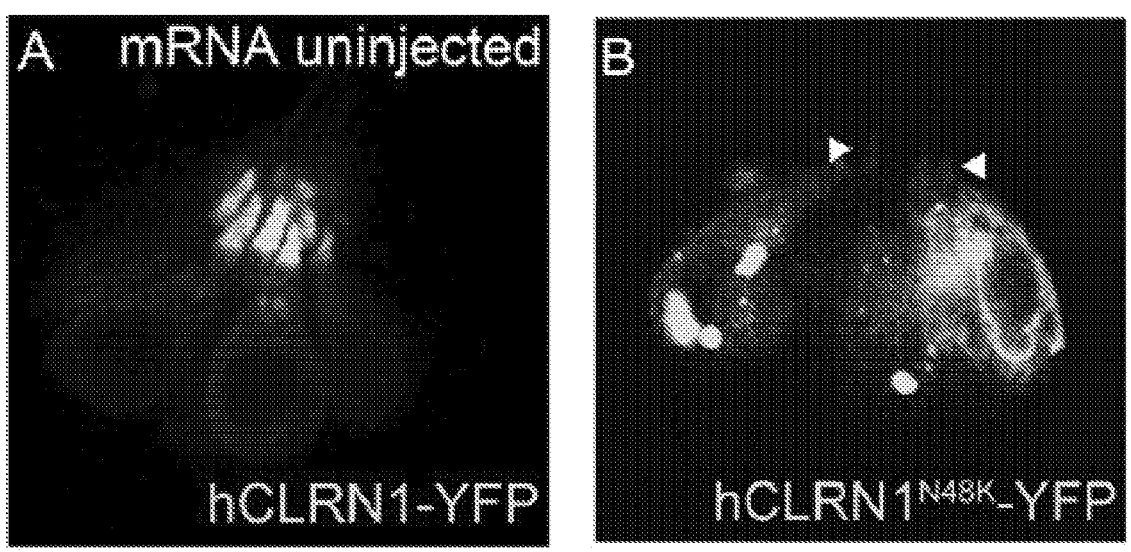
FIGS. 3(A-G) illustrate images and a graph showing hGRASP55 expression enhances hair bundle localization of hCLRN1$^{N48K}$. Single-cell stage embryos from clrn1$^{+/+}$ parents stably expressing hCLRN1$^{N48K}$-YFP in hair cells were injected with hGRASP55 mRNA or hSNX27 mRNA to induce transient expression of hGRASP55 or hSNX27, unconventional protein sorting pathway cargo proteins in the developing embryo. At 5 dpf, hair cells in the neuromast were observed for changes in the expression pattern of hCLRN1$^{N48K}$-YFP (n=20, number of larvae examined per group). Representative images are shown here. Neuromast hair cells from uninjected, stable transgenic line expressing hCLRN1-YFP (A) or hCLRN1$^{N48K}$-YFP (B) in the clrn1$^{+/+}$ background served as reference controls. Compared to the uninjected control (arrowhead, B), transient expression of hGRASP55 increased the amount of hCLRN1$^{N48K}$-YFP reaching the hair bundle as reflected by increased intensity of YFP signal in the bundle (arrow, C and D) Magnification, 40×. And no difference in the intensity of hCLRN1$^{N48K}$-YFP in larvae transiently expressing hSNX27 (arrowhead, E and F). All images captured from live larvae and all images shown here are 1 μM single plane images. (G) Quantification of YFP intensity in the bundle using image J software. The ****p value<0.0001.
Figure 3G:
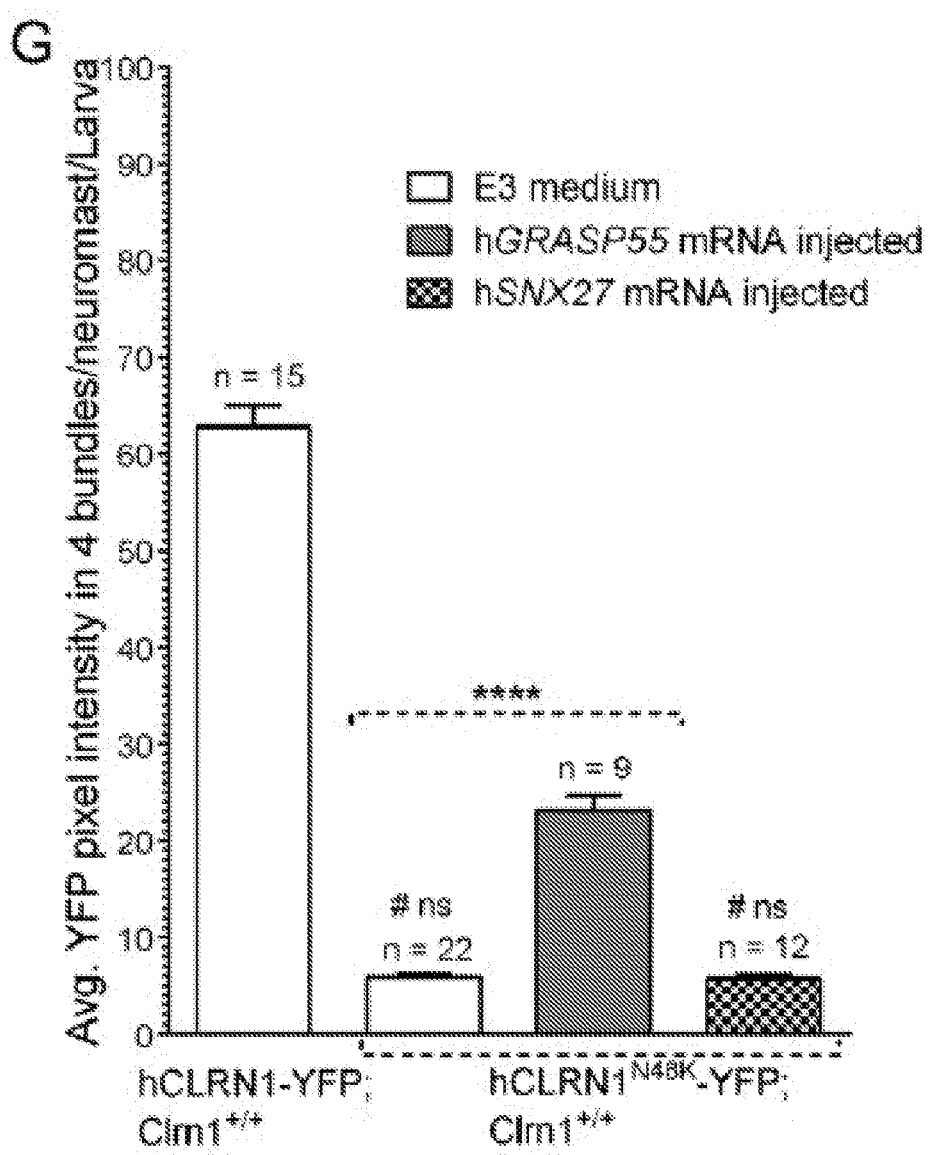

Unconventional Protein Secretory Pathway Cargo (hGRASP55) Expression Enhances Hair Bundle Localization of hCLRN1$^{N48K}$ Mutant Protein The N-glycan in the membranous N-glycoprotein is the signal for protein folding and conventional trafficking of these proteins to the plasma membrane. Loss of Nglycosylation site in N-glycoprotein results in misfolding and intracellular retention of the mutant protein. Accumulation of misfolded protein in the ER triggers ERAD of the mutant protein as well as ER stress signals. ER stress signals activate Golgi-independent trafficking of membrane proteins. We hypothesize that the normal hearing by birth in the USH3-CLRN1$^{N48K}$ individuals could be due to a small proportion of ER-retained hCLRN1$^{N48K}$ in developing hair cells "escapes" ERAD and reaches the plasma membrane via Golgi-independent or unconventional trafficking pathway to retain hair bundle structure and hair cell function. There are examples of unconventional trafficking of the mutant protein involved in monogenic disorders. For example, the cargo proteins, hGRASP55 is known to help ER trapped proteins like ΔF508 CFTR in trafficking to the plasma membrane via Golgi independent unconventional pathway and hSNX27, reported to be involved in the plasma membrane trafficking of the ER trapped misfolded membrane proteins loaded to endosomes that are programmed to undergo lysosomal degradation. In this study, we tested whether these two cargo proteins: hGRASP55 and hSNX27, which specifically play a role in sorting internalized misfolded transmembrane proteins with PDZ type I domain binding site (PDB-type I) to the plasma membrane through different unconventional secretory pathways under special conditions like unfolded protein response (UPR) triggered up-regulation of ER stress signal, can rescue hCLRN1$^{N48K}$ protein with PDZ domain type I binding site to the plasma membrane and hair bundles. Single-cell stage embryos from zebrafish hCLRN1$^{N48K}$-YFP; clrn1$^{+/+}$ stable line were either injected with hGRASP55 mRNA or hSNX27 mRNA to induce transient expression of hGRASP55 or hSNX27 in the developing embryo. At 4 dpf, hair cells in the neuromast of hGRASP55 mRNA injected larvae and hSNX27 mRNA injected larvae were observed live for changes in the expression pattern of hCLRN1$^{N48K}$-YFP in the bundle and cell body of the hCLRN1$^{N48K}$-YFP; clrn1$^{+/+}$ hair cells [Number of injected larvae examined per group (n)=25]. In the hGRASP55 mRNA injected group nine out of 25 larvae showed significant increase in the YFP intensity in the hair bundles compared to the uninjected hCLRN1$^{N48K}$-YFP; clrn1$^{+/+}$ hair cells, whereas the difference in the intensity of YFP in hair bundles of examined hSNX27 mRNA injected larvae were indistinguishable from the uninjected hCLRN1$^{N48K}$-YFP; clrn1$^{+/+}$ larvae. Representative images from hGRASP55 mRNA injected (FIGS. 3C-3D) and hSNX27 mRNA injected (FIGS. 3E-3F) groups are shown here. Neuromast hair cells from uninjected, stable transgenic line expressing hCLRN1-YFP (FIG. 3A) or hCLRN1$^{N48K}$-YFP (FIG. 3B) in the clrn1$^{+/+}$ background served as reference controls. Only, those nine hGRASP55 mRNA injected hCLRN1$^{N48K}$-YFP; clrn1$^{+/+}$ larvae that showed significant increase in hCLRN1$^{N48K}$-YFP localization in the hair bundle were considered for the quantification of change in YFP intensity level in the hair bundles using ImageJ software (Schneider et al., 2012). Since, no difference was observed in the hair bundle YFP intensity from hSNX27 mRNA injected group in comparison to the uninjected hCLRN1$^{N48K}$-YFP; clrn1$^{+/+}$ group, a random pick of 12 hSNX27 mRNA injected hCLRN1$^{N48K}$-YFP; clrn1$^{+/+}$ larvae were considered for quantification of the YFP intensity in the hair bundles. We quantified the amount of hCLRN1$^{N48K}$-YFP rescued to the hair bundle by estimating the increase in count of YFP pixel intensity in unadjusted fixed triangle shaped ROI covering the cone shaped area of hair bundle in 1 micron middle section of hair bundle from 2 of O and 2 of MI position anterior lateral line (ALL) neuromast hair cells from hCLRN1$^{N48K}$-YFP; clrn1$^{+/+}$ larvae either uninjected or injected 20 with the unconventional pathway cargo protein's mRNA (hGRASP55 or hSNX27). Compared to the uninjected hCLRN1$^{N48K}$-YFP; clrn1$^{+/+}$ control (FIG. 3B), transient expression of hGRASP55 significantly increased the amount of hCLRN1$^{N48K}$-YFP reaching the hair bundle as reflected by increased intensity of YFP signal in the bundle (Number of hGRASP55 injected hair cell bundles (ROI) analyzed for change in YFP intensity (n)=33; Cumulative average of YFP intensity in the ROI from total number of hair bundles considered for quantification in hGRASP55 mRNA injected group=23.12±1.56; Number of hair bundles analyzed to generate basal level of YFP intensity from age match hCLRN1$^{N48K}$-YFP; clrn1$^{+/+}$ larvae (n)=84; Basal YFP intensity=5.927±0.32, Mean±SEM; FIGS. 3C, 3D and 3G). Whereas, the endosome to plasma membrane sorting cargo hSNX27, failed to enhance the surface or bundle expression of the mutant hCLRN1$^{N48K}$-YFP protein (Number of hair bundles analyzed (n)=48; Cumulative average of YFP intensity in the ROI of hair bundles from hSNX27 mRNA injected group=5.745±0.419, Mean±SEM; FIGS. 3E, 3F and 3G). The observed level of YFP intensity at ROI in the hair bundles of hCLRN1$^{N48K}$-YFP; clrn1$^{+/+}$ larvae injected with hGRASP55 mRNA was 4 fold increase compared to uninjected or hSNX27 mRNA injected groups (FIG. 3G). This confirms that at younger age the ER trapped misfolded hCLRN1$^{N48K}$ mutant protein are transported to the hair bundle by hGRASP55 dependent unconventional secretory pathway and not through hSNX27 dependent unconventional secretory pathway.

SERCA Inhibitors TG and ART are Potent Rectifiers of hCLRN1$^{N48K}$ Mutant Protein Phenotype We then took a biochemical approach to independently verify the mechanism of transport of hCLRN1$^{N48K}$ by GRASP-mediated unconventional secretory pathway in hair cells. It has been suggested that the selective activation of GRASP55 dependent unconventional trafficking pathway is a potential therapeutic strategy for the treatment of diseases arising from transport defects of misfolded proteins. GRASP55 dependent unconventional protein secretion pathway can be activated by phosphorylation of the GRASP55 protein through downstream ER stress signaling pathways induced by ER unfolded protein response (UPR). The sarco/endoplasmic reticulum $Ca^{2+}$-ATPase (SERCA) inhibitors: Thapsigargin (TG), anticancer drug and Artemesinin (ART), anti-malarial drug are two different sesquiterpene lactones (SQL), perturbs ER function by depleting ER luminal calcium stores, are also a well-known agent that induces UPR in mammalian cells (Pahl, 1999), known to induce GRASP55 dependent unconventional secretory pathway (Gee et al., 2011; REFs for ART). Comparatively, TG is a stronger inhibitor of SERCA pump than ART based on the difference in their SERCA binding site. TG induces UPR associated upregulation of one of the three ER stress signals, IRE1α that activates ERK/MEK signaling pathway. ERK/MEK signaling pathway in turn phosphorylates GRASP55 and relocalize it into the ER, resulting in activation of GRASP55 mediated unconventional protein secretion. Here we tested whether treating the hCLRN1$^{N48K}$ mutant zebrafish with SERCA inhibitors capable of inducing release of ER retained misfolded hCLRN1$^{N48K}$ mutant protein and enhance its trafficking to the hair 22 cell plasma membrane and hair bundle. In this drug screening study, 3 dpf old transgenic larvae from the following genotypes, hCLRN1 N-glycosylation site mutant (hCLRN1-YFP; clrn1$^{+/+}$) and wild-type hCLRN1 (hCLRN1$^{N48K}$-YFP; clrn1$^{+/+}$) were used (25 larvae/genotype/drug dosage/treatment duration). The TG and ART dosages used in this study were determined based on earlier reported non-lethal dosages of these drugs proven to perturb ER $Ca^{2+}$ level and trigger unconventional protein secretory pathway. We captured live confocal image of neuromast hair cells from the treated and untreated groups using YFP filter to quantify the amount of hCLRN1$^{N48K}$-YFP protein rescue to the hair bundles of neuromast hair cells at various time points starting from 1 hr to overnight, respectively. In comparison to the quantity of hCLRN1$^{N48K}$-YFP in the untreated hair bundles, the maximum level of rescued hCLRN1$^{N48K}$-YFP in the hair bundles were observed in the 1 μM TG dosage group at 4 hours of treatment (FIGS. 4A-C and 4E-G). TG dosages lower than 1 μM were inefficient in rescuing mutant protein and the dosages higher than 1 μM or longer treatment duration were found to be lethal. At a lower dosage level of ART (0.4 μM) compared to best rescue level dosage in TG (1 μM) treatment group, we observed comparatively significant increase in the expression of the hCLRN1$^{N48K}$-YFP protein in the hair bundle of ART treated group (FIGS. 4H and 4I-J). Maximum number of hair bundles with the strong expression of hCLRN1$^{N48K}$-YFP protein was observed in the ART treated group (76%) than in TG treated group (38%) compared to hair bundles from untreated hCLRN1$^{N48K}$-YFP hair cells (<5%; FIG. 4I). The amount of protein rescued to the hair bundle was quantified in 23 terms of difference in the YFP intensity in the hair bundles of treated and untreated groups using ImageJ software. In average, 4 bundles per ML1 neuromast per larvae from each treatment groups were considered for YFP intensity quantification. Number of hair bundles considered for YFP intensity quantification in, Group-1: hCLRN1$^{N48K}$-YFP; clrn1$^{+/+}$ larvae treated with 1 uM TG+0.01% DMSO in E3 medium (n)=46, and cumulative average of YFP intensity in the ROI in hair bundles from TG treated group=18.59±0.87; Group-2: hCLRN1$^{N48K}$-YFP; clrn1$^{+/+}$ larvae treated with 0.4 uM ART+0.01% DMSO in E3 medium (n)=44, and cumulative average of YFP intensity in the ROI in hair bundles from ART treated group=31.04±1.25; Group-3: hCLRN1$^{N48K}$YFP; clrn1$^{+/+}$ larvae treated with 0.01% DMSO in E3 medium (n=80)=5.67±0.32; Group-4: Untreated hCLRN1$^{N48K}$-YFP; clrn1$^{+/+}$ larvae in E3 medium (n=84)=5.927±0.32; Group-5: hCLRN1-YFP; clrn1$^{+/+}$ larvae in E3 medium (n=30)=62.82±2.15; Group-6: hCLRN1-YFP; clrn1$^{+/+}$ larvae treated with 0.01% DMSO in E3 medium (n=30)=61.29±2.05; Group-7: hCLRN1-YFP; clrn1$^{+/+}$ larvae treated with 1 uM TG+0.01% DMSO in E3 medium (n=30)=68.57±1.36; and Group-8: hCLRN1-YFP; clrn1$^{+/+}$ larvae treated with 0.4 uM ART+0.01% DMSO in E3 medium (n=30)=71.32±2.05 [Mean±SEM; FIGS. 4A-C and 4E-G]. The hCLRN1$^{N48K}$-YFP; clrn1$^{+/+}$ larvae treated with TG or ART resulted in increase in trafficking of hCLRN1$^{N48K}$ to the hair bundle by 3 and 5 folds, respectively. Notably, treating the hCLRN1-YFP; clrn1$^{+/+}$ larvae with TG or ART and vehicle (0.01% DMSO) did not affect the pattern of localization of the wild-type hCLRN1-YFP to the hair cell's bundle or plasma membrane (FIGS. 4A-D).

These results from genetic and chemo approaches confirms that perturbing ER $Ca^{2+}$ levels by blocking the SERCA channel in the ER lumen enhances the expression of hCLRN1$^{N48K}$-YFP mutant protein level in the hair bundle by releasing the ER trapped mutant protein and trafficking through hGRASP55 dependent unconventional protein secretory pathway. The difference in the rescue level observed in the ART group than in the TG group, suggests that moderately perturbing ER $Ca^{2+}$ level is good enough to achieve the maximum rescue of hCLRN1$^{N48K}$-YFP mutant protein to the hair bundle.

On the other hand from the hCLRN1$^{N48K}$-YFP; clrn1$^{KO/KO}$ zebrafish generated in this study, we came to know that hCLRN1$^{N48K}$-YFP is functional and if trafficked to the bundle it was able to restore the cone shape hair bundle structure. The hCLRN1$^{N48K}$YFP; clrn1$^{KO/KO}$ zebrafish showed progressive loss of hair cell function. And from the SERCA inhibitors based therapy experiments, it is shown here that the treatment with SERCA inhibitors TG and ART, improved 3 and 5 folds increase in the bundle localization of the hCLRN1$^{N48K}$-YFP, respectively. Next, it is important to know whether these SERCA inhibitors will, 1) improve the hair cell function, and 2) prevent the progressive loss of hair cell function caused by gradual reduction in the trafficking of hCLRN1$^{N48K}$ protein to the hair bundle due to constant degradation of misfolded mutant hCLRN1$^{N48K}$ in ER through ERAD, and helps in sustaining the hair cell function for longer than that observed in the untreated hCLRN1$^{N48K}$-YFP; clrn1$^{KO/KO}$ group. To test this hypothesis, we treat the hCLRN1$^{N48K}$-YFP; clrn1$^{KO/KO}$ larvae with 0.4 μM ART for 4 hours/day for consecutive 4 days starting from 3 dpf to 6 dpf with (ART was selected for treatment in this study, since it in comparison to 1 μM TG showed better rescue level of hCLRN1$^{N48K}$-YFP to hair bundle), followed by extracellular microphonics potential recording from the hair cells of ML1 neuromast at 6 dpf. At 6 dpf, hCLRN1$^{N48K}$-YFP positive clrn1$^{KO/KO}$ hair cells from the 0.4 μM ART treated hCLRN1$^{N48K}$-YFP; clrn1$^{KO/KO}$ 25 larvae with cone-shaped hair bundles were tested for microphonic potentials to identify whether the ART treatment depended 5 fold increase in the amount of hCLRN1$^{N48K}$ trafficked to the hair bundle helps in improve mechanotransduction (amplitude in Microphonics recording) comparative to that recorded from the untreated hCLRN1$^{N48K}$YFP; clrn1$^{KO/KO}$ larvae. The extracellular microphonic potentials were recorded from hair cells of two neuromasts/larvae from seven ART treated and untreated hCLRN1$^{N48K}$YFP; clrn1$^{KO/KO}$ zebrafish larvae (FIGS. 5A-5C). The recorded extracellular microphonic potentials from clrn1$^{KO/KO}$ mutants was 3.966 V±0.76 (Mean±SEM), clrn1$^{+/+}$ was 11.93 V±0.98 (Mean±SEM), untreated hCLRN1$^{N48K}$-YFP; clrn1$^{KO/KO}$ larvae was 7.286 V±0.744 (Mean±SEM), untreated hCLRN1-YFP; clrn1$^{KO/KO}$ larvae was 10.12 V±0.803 (Mean±SEM), and 0.4 uM ART treated hCLRN1$^{N48K}$-YFP; clrn1$^{KO/KO}$ larvae was 9.529 V±0.803 (Mean±SEM). The difference in potentials recorded from hCLRN1$^{N48K}$-YFP; clrn1$^{KO/KO}$ hair cells compared to the clrn1$^{+/+}$ hair cells and hCLRN1-YFP; clrn1$^{KO/KO}$ hair cells were not significant (p>0.05; FIG. 5A). Confirming that the improvement in the hair cell function from ART treated hCLRN1$^{N48K}$-YFP; clrn1$^{KO/KO}$ larvae were comparable to that of clrn1$^{+/+}$ and hCLRN1-YFP; clrn1$^{KO/KO}$ larvae.

To verify the degree of overall rescue in swimming behavior (hair cell function) and prolongation of life span by ART treatment in the hCLRN1$^{N48K}$-YFP; clrn1$^{KO/KO}$ zebrafish larvae, survival rate, swimming behavior and startle response were observed longitudinally from 6.5 to 27 dpf (Table 1). For this rescue experiment, we followed two regimens of ART treatment. Regimen I, 35 larvae from hCLRN1$^{N48K}$-YFP; clrn1$^{KO/KO}$ genotype were treated with 0.4 uM ART from 3 to 7 dpf (5 days of treatment during inner ear development and hair cell maturation). Regimen II, 20 larvae from hCLRN1$^{N48K}$-YFP; clrn1$^{KO/KO}$ genotype were treated with 0.4 uM ART from 3 to 12 dpf (10 days of treatment overlapping development and post-development of inner ear anatomy and hair cell maturation). At 6.5 dpf, the swimming behavior and startle response of hCLRN1$^{N48K}$-YFP; clrn1$^{KO/KO}$ larvae from ART treatment regimen I and II, were indistinguishable from that of clrn1$^{+/+}$ and hCLRN1-YFP; clrn1$^{KO/KO}$ larvae. About 75% (Regimen I+II: 41 larvae) of ART treated hCLRN1$^{N48K}$-YFP; clrn1$^{KO/KO}$ larvae had clrn1$^{+/+}$ equivalent startle response. In regimen I and II, the survival rate and swimming behavior of hCLRN1$^{N48K}$-YFP; clrn1$^{KO/KO}$ larvae beyond 25 dpf shown significant improvement from 5% in untreated hCLRN1$^{N48K}$-YFP; clrn1$^{K}$ larvae to 40% (n=14) and 45% (n=45%), respectively. This indicates that ART treatment protected and further delayed hair cells deterioration associated with the misfolded hCLRN1$^{N48K}$ aggregation in ER induced hair cell loss in the hCLRN1$^{N48K}$-YFP; clrn1$^{KO/KO}$ larvae (Table 1). Overall, result confirms that ART is not only able to correct the trafficking defect of hCLRN1$^{N48K}$ protein, but also able to help in normal hair cell functioning of hair cells from hCLRN1$^{N48K}$YFP; clrn1$^{KO/KO}$ zebrafish and delay onset progressive loss of hair cell function. This suggest that it is possible to protect the hearing in USH3-CLRN1$^{N48K}$ individuals by treating with anti-malarial drug ART in their early stage of onset in progression of hearing loss.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of treating a glycosylation-defective protein associated disease or disorder in a subject in need thereof, the method comprising:
   administering to the subject a therapeutically effective amount of a Sarco/ER ATPase (SERCA) inhibitor.

2. The method of claim 1, the SERCA inhibitor selected from the group consisting of Artemisinin, Artesunate (Arts), thapsigargin, mipsagargin, DBHQ (2,5-di-tert-butylhydroquinone), Saikosaponin-d (Ssd), SBF-1, ruthenium red, curcumin, F36, gingerol, paxilline, cyclopiazonic acid, sHA14-1, CXL017, and analogs thereof.

3. The method of claim 2, the SERCA inhibitor comprising Artesunate (Arts).

4. The method of claim 1, wherein the therapeutically effective amount is the amount required to increase cytosolic calcium levels and perturb ER in cells of the subjects.

5. The method of claim 1, wherein the therapeutically effective amount is an amount effective to potentiate ER stress and unfolded protein response (UPR) in cells of the subjects.

6. The method of claim 1, the glycosylation-defective protein associated disease or disorder is a human clarin-1 protein (hCLRN1) defect related disease or disorder.

7. The method of claim 6, the hCLRN1 defect related disease or disorder comprising a hCLRN1$^{N48K}$ missense mutation related disease or disorder.

8. The method of claim 7, the hCLRN1$^{N48K}$ missense mutation related disease or disorder comprising Usher syndrome type III (USH3).

9. A method of treating a sensory deficit in a subject associated with a mutation of the human clarin-1 protein hCLRN1 protein, the method comprising:
   administering to the subject a therapeutically effective amount of a Sarco/ER ATPase (SERCA) inhibitor.

10. The method of claim 9, the sensory deficit comprising hearing loss.

11. The method of claim 10, the therapeutically effective amount comprising an amount effective to promote hCLRN1$^{N48K}$ localization to hair bundles of a hair cell.

12. The method of claim 9, the SERCA inhibitor selected from the group consisting of Artemisinin, Artesunate (Arts), thapsigargin, mipsagargin, DBHQ (2,5-di-tert-butylhydroquinone), Saikosaponin-d (Ssd), SBF-1, ruthenium red, curcumin, F36, gingerol, paxilline, cyclopiazonic acid, sHA14-1, CXL017, and analogs thereof.

13. The method of claim 9, the SERCA inhibitor comprising Artesunate (Arts).

14. The method of claim 9, wherein the SERCA inhibitor is administered prior to sensory deficit in a subject.

15. The method of claim 9, the sensory deficit associated with the $^{N48K}$ destabilizing missense mutation in the human clarin-1 protein (hCLRN1$^{N48K}$).

16. A method of treating Usher syndrome type III (USH3) in a subject, the method comprising:
   administering to the subject a therapeutically effective amount of a Sarco/ER ATPase (SERCA) inhibitor.

17. The method of claim 16, wherein USH3 is associated with a human clarin-1 protein (hCLRN1) missense mutation.

18. The method of claim 17, the hCLRN1 missense mutation comprising hCLRN1$^{N48K}$.

19. The method of claim 16, the SERCA inhibitor selected from the group consisting of Artemisinin, Artesunate (Arts), thapsigargin, mipsagargin, DBHQ (2,5-di-tert-butylhydroquinone), Saikosaponin-d (Ssd), SBF-1, ruthenium red, curcumin, F36, gingerol, paxilline, cyclopiazonic acid, sHA14-1, CXL017, and analogs thereof.

20. The method of claim 19, the SERCA inhibitor comprising Artesunate (Arts).

21. The method of claim 16, the therapeutically effective amount comprising an amount effective to promote hCLRN1$^{N48K}$ localization to hair bundles of a hair cell.

22. The method of claim 16, wherein the SERCA inhibitor is administered prior to sensory deficit in the USH3 subject.

* * * * *